(12) United States Patent
Engelbart et al.

(10) Patent No.: US 7,193,696 B2
(45) Date of Patent: Mar. 20, 2007

(54) SYSTEMS AND METHODS FOR USING LIGHT TO INDICATE DEFECT LOCATIONS ON A COMPOSITE STRUCTURE

(75) Inventors: Roger W. Engelbart, St. Louis, MO (US); Frank Gregory Speno, Glendale, MO (US)

(73) Assignee: United Technologies Corporation, Hartford, CT (US)

( * ) Notice: Subject to any disclaimer, the term of this patent is extended or adjusted under 35 U.S.C. 154(b) by 310 days.

(21) Appl. No.: 10/822,538

(22) Filed: Apr. 12, 2004

(65) Prior Publication Data
US 2005/0225753 A1 Oct. 13, 2005

(51) Int. Cl.
*G01N 21/88* (2006.01)
(52) U.S. Cl. ................. 356/237.1; 356/237.2
(58) Field of Classification Search ............. 356/237.1, 356/237.2
See application file for complete search history.

(56) References Cited

U.S. PATENT DOCUMENTS

| | | | |
|---|---|---|---|
| 3,879,245 A | 4/1975 | Fetherson et al. | |
| 4,064,534 A | 12/1977 | Chen et al. | |
| 4,310,132 A | 1/1982 | Frosch et al. | |
| 4,548,859 A | 10/1985 | Kline et al. | |
| 4,608,220 A | 8/1986 | Caldwell et al. | |
| 4,693,678 A | 9/1987 | Von Volkli | |
| 4,699,683 A | 10/1987 | McCowin | |
| 4,760,444 A | 7/1988 | Nielson et al. | |
| 4,780,262 A | 10/1988 | Von Volkli | |
| 4,790,898 A | 12/1988 | Woods | |
| 4,830,298 A | 5/1989 | Van Blunk | |
| 4,877,471 A | 10/1989 | McCowin et al. | |
| 4,941,182 A | 7/1990 | Patel | |
| 5,024,399 A | 6/1991 | Barquet et al. | |
| 5,058,497 A | 10/1991 | Bishop et al. | |

(Continued)

FOREIGN PATENT DOCUMENTS

EP 0 319 797 6/1989

(Continued)

OTHER PUBLICATIONS

U.S. Appl. No. 10/846,974, entitled Systems and Methods for Identifying Foreign Objects and Debris (FOD) and Defects During Fabrication of a Composite Structure, Engelbart et al., filed May 14, 2004.

(Continued)

*Primary Examiner*—Richard A. Rosenberger
(74) *Attorney, Agent, or Firm*—Harness, Dickey & Pierce, P.L.C.

(57) ABSTRACT

A method for using light to indicate locations of flaws and defects on a composite structure generally includes electronically accessing positional data defining one or more defect locations on a composite structure. The positional data can be extracted from a part fabrication file in which resides numerical control (NC) data that can be used by a material placement machine to fabricate the composite structure. The method also includes automatically causing at least one light source to direct light at the composite structure to indicate the defect locations as defined by the positional data. Accordingly, the light allows the defect locations to be readily ascertained for later action, such as manual defect repair and/or FOD removal by an operator.

26 Claims, 16 Drawing Sheets

U.S. PATENT DOCUMENTS

| | | | |
|---|---|---|---|
| 5,153,668 A | 10/1992 | Katzir et al. ............. | 356/237.2 |
| 5,198,983 A | 3/1993 | Blake et al. | |
| 5,337,647 A | 8/1994 | Roberts et al. | |
| 5,439,549 A | 8/1995 | Fryc et al. | |
| 5,450,147 A | 9/1995 | Dorsey-Palmateer | |
| 5,518,208 A | 5/1996 | Roseburg | |
| 5,540,126 A | 7/1996 | Piramoon | |
| 5,562,788 A | 10/1996 | Kitson et al. | |
| 5,651,600 A | 7/1997 | Dorsey-Palmateer | |
| 5,683,646 A | 11/1997 | Reiling, Jr. | |
| 5,700,337 A | 12/1997 | Jacobs et al. | |
| 5,746,553 A | 5/1998 | Engwall | |
| 5,804,276 A | 9/1998 | Jacobs et al. | |
| 5,814,386 A | 9/1998 | Vasiliev et al. | |
| 5,822,055 A | 10/1998 | Tsai et al. ................. | 356/237.1 |
| 5,825,495 A | 10/1998 | Huber | |
| 5,871,117 A | 2/1999 | Protasov et al. | |
| 5,917,588 A | 6/1999 | Addiego | |
| 5,949,901 A | 9/1999 | Nichani et al. ............. | 382/149 |
| 5,963,660 A | 10/1999 | Koontz et al. | |
| 5,979,531 A | 11/1999 | Barr et al. | |
| 6,012,883 A | 1/2000 | Engwall et al. | |
| 6,013,341 A | 1/2000 | Medvedev et al. | |
| 6,045,651 A | 4/2000 | Kline et al. | |
| 6,074,716 A | 6/2000 | Tsotsis | |
| 6,075,883 A | 6/2000 | Stern et al. ................. | 382/144 |
| 6,086,696 A | 7/2000 | Gallagher | |
| 6,112,792 A | 9/2000 | Barr et al. | |
| 6,168,358 B1 | 1/2001 | Engwall et al. | |
| 6,205,239 B1 | 3/2001 | Lin et al. | |
| 6,288,780 B1 | 9/2001 | Fairley et al. ........... | 356/237.1 |
| 6,364,250 B1 | 4/2002 | Brinck et al. | |
| 6,369,492 B1 | 4/2002 | Sugimoto | |
| 6,390,169 B1 | 5/2002 | Johnson | |
| 6,451,152 B1 | 9/2002 | Holmes et al. | |
| 6,480,271 B1 | 11/2002 | Cloud et al. | |
| 6,639,660 B1* | 10/2003 | Beck et al. .............. | 356/237.2 |
| 6,648,273 B2 | 11/2003 | Anast | |
| 6,692,681 B1 | 2/2004 | Lunde | |
| 6,725,123 B1 | 4/2004 | Denuell | |
| 6,799,619 B2 | 10/2004 | Holmes et al. | |
| 6,937,753 B1 | 8/2005 | O'Dell et al. ................ | 382/141 |
| 7,039,485 B2* | 5/2006 | Engelbart et al. ........... | 700/110 |
| 2001/0002149 A1 | 5/2001 | Vaez-Iravani et al. | |
| 2001/0023349 A1 | 9/2001 | Van Tassel et al. | |
| 2002/0141632 A1 | 10/2002 | Engelbart et al. | |
| 2005/0030527 A1 | 2/2005 | Reinhorn ................. | 356/237.2 |

FOREIGN PATENT DOCUMENTS

| | | |
|---|---|---|
| EP | 0 833 146 | 4/1998 |
| EP | 0903574 | 3/1999 |
| EP | 1 030 172 | 8/2000 |
| JP | 2001012930 | 1/2001 |
| WO | WO 94/18643 | 8/1994 |
| WO | WO 2004/025385 | 3/2004 |

OTHER PUBLICATIONS

Pending U.S. Appl. No. (not yet assigned) entitled Composite Barrel Sections for Aircraft Fuselages and Other Structures, and Methods and Systems for Manufacturing Such Barrel Sections, Biornstad, filed May 20, 2004.

Fiedler, L., et al, "Tango Composite Fuselage Platform", SAMPE Journal, vol. 39, No. 1, Jan./Feb. 2003, pp. 57-63.

BAe 146, Flight International, May 2, 1981, 2 pages.

A Barrelful of Experience, Intervia, May 1992, 2 pages.

Raytheon, Mar. 2000, vol. 4, No. 2, http://www.cts.com/king/vasci/newsletter/vol42.html.

Business Aviation, Jun. 7, 2002, http://www.aviationnow.com/avnow/news/channel_busav.jsp?view=story&id=news/btoyo0607.xml.

Beechcraft's Composit Challenge, http://www.aerotalk.com/Beech.cfm.

Evans, Don O., "Fiber Placement", 3 pages, Cincinnati Machine, pp. 477-479.

Pending U.S. Appl. No. 60/559,911, Johnson et al., filed Apr. 4, 2004.

Pending U.S. Appl. No. 60/559,890, Biornstad et al., filed Apr. 6, 2004.

Pending U.S. Appl. No. 10/819,084, Turnmire et al.

Pending U.S. Appl. No. 10/853,075, Johnson et al.

Pending U.S. Appl. No. 10/949,848, Stulc, filed Sep. 23, 2004.

Advanced Technology Tape Laying for Affordable Manufacturing of Large Composite Structures; http://www.cinmach.com/tech/pdf/TapeLayingGrimshaw.pdf; Michael N. Grimshaw, et al; 11 pages.

Fiber Placement; http://www.cinmach.com/tech/pdf/asm_chapter_fp.pdf; Don O. Evans; Cincinnati Machine; 3 pages.

Automated Tape Laying; http://www.cinmach.com/tech/pdf/Grimshaw%20ASM%20Handbook.pdf; Michael N. Grimshaw; Cincinnati Machine; 6 pages.

Raytheon Aircraft's Hawker Horizon Reaches Fuselage Milestone, Raytheon News Release; http://www.beechcraft.de/Presse/2000/100900b.htm; 2 pages.

European Search Report, Application No. 04076900.2, dated Dec. 1, 2004, 4 pages.

Prof. J. Zhang: "Angewandte Sensorik" CH. 4, Sensoren in der Robotik, Nov. 11, 2003, pp. 76-113, XP002327793; URL:http://tech-www.informatik.uni-hamburg.de/lehre/ws2003/vorlesungen/angewandte_sensorik/vorlesung_03.pdf>, retrieved on Apr. 2004, p. 89.

Krupka R; Walz T; Ettemeyer A: "Industrial applications of shearography for inspection of aircraft components" Proceedings of the 8th European Conference of Nondestructive Testing, Barcelona (Spain), Jun. 17-21, 2002, 'Online! Jun. 30, 2002, XP002351899 NDT.NET—Feb. 2003, vol. 8, No. 2 Retrieved from the Internet: URL:http://www.ndt.net/article/ecndt02/484/484.htm> 'retrieved on Oct. 31, 2005!.

U.S. Appl. No. 10/068,735, entitled Composite Material Collation Machine and Associated Method for High Rate Collation of Composite Materials, filed Feb. 6, 2002, Engelbart et al.

U.S. Appl. No. 10/217,805, entitled System for Identifying Defects in a Composite Structure, filed Aug. 13, 2002, Engelbart et al.

U.S. Appl. No. 10/301,949, entitled Parallel Configuration Composite Material Fabricator, Engelbart et al., filed Nov. 22, 2002.

U.S. Appl. No. 10/628,691, entitled Systems and Methods for Identifying Foreign Objects and Debris (FOD) and Defects During Fabrication of a Composite Structure, filed Jul. 28, 2003, Engelbart, et al.

U.S. Appl. No. 10/630,594, entitled Composite Fuselage Machine, Braun, filed Jul. 28, 2003.

U.S. Appl. No. 10/646,316, entitled Unidirectional Multihead Fiber Placement, New, filed Aug. 22, 2003.

U.S. Appl. No. 10/646,392, entitled Automated Composite Lay-Up to an Internal Fuselage Mandrel, Engwall, filed Aug. 22, 2003.

U.S. Appl. No. 10/646,509, entitled Multiple Head Automated Composite Laminating Machine for the Fabrication of Large Barrel Section Components, Johnson, Aug. 22, 2003.

U.S. Appl. No. 10/664,148, entitled Composite Material Collation Machine and Associated Method for High Rate Collation of Composite Materials; divisional U.S. Appl. No. 10/068,735, filed Sep. 17, 2003, Engelbart, et al.

U.S. Appl. No. 10/717,030, entitled Method of Transferring Large Uncured Composite Lamintes, Johnson, filed Nov. 18, 2003.

U.S. Appl. No. 10/726,099, entitled Systems and Methods for Determining Defect Characteristics of a Composite Structure, Engelbart et al., filed Dec. 2, 2003.

U.S. Appl. No. 10/799,306, entitled Systems and Methods for Enabling Automated Return to and/or Repair of Defects With a Material Placement Machine, Engelbart et al., filed Mar. 12, 2004.

Sharp et al.; "*Material Selection/Fabrication Issues for Thermoplastic Fiber Placement*", Journal of Thermosplastic Composite Materials, vol. 8; Jan. 1995, p. 2-14.

http://www.cinmach.com/WolfTracks4_1/MTG_WT7.htm; Premier I Features Lighter, Stronger All-Composite Fuselage, 3 pages.

http://www.cinmach.com/compnews/PressReleases/pr00-11.htm; Raytheon Aircraft Orders Four More Fiber Cincinnati Fiber Placement Systems for Industry's First Composite-Fuselage Business Jets, 2 pages.

http://www.rockymountaincomposites.com/wind_sys.htm; Filament Winding, 2 pages.

Bruckstein et al., "Omniview Cameras With Curved Surface Mirrors", Jun. 12, 2000, IEEE Omnidirectional Vision Proceedings, pp. 79-84.

* cited by examiner

```
N75G67X-21.0014Y24.256Z-40.3284H-.523185H.625822H-.578467D.475303D.77768D.411462 T[ ] L.2105 R.2278$
N76G67X-20.9694Y24.3135Z-40.3008H-.520986H.626242H-.579996D.476623D.777133D.410967 L.0691 R.0748$
N77G67X-20.7996Y24.6094Z-40.1583H-.510021H.627664H-.588147D.482329D.774838D.408639 L.3593 R.3871$
N78G67X-20.5445Y25.0405Z-39.9483H-.495813H.627241H-.600615D.495996D.772242D.397027 L.5235 R.5492$
N79G67X-20.1859Y25.6163Z-39.6704H-.489899H.602916H-.629676D.482231D.789137D.380416 L.7311 R.7653$
N80G67X-19.8706Y26.1118Z-39.4231H-.471868H.602715H-.643487D.494341D.785198D.372949 L.6196 R.6529$
N81G67X-19.5431Y26.6058Z-39.1746H-.455301H.599345H-.658396D.494171D.785243D.37308 L.6296 R.6666$
```

G64.4X-32.7956Y44.051Z-39.1746H-.455301H.599345H-.658396D.494171D.785243D.37308 F400$
G64.3X-46.0181Y29.9728Z-41.489H-.837935H.54577H0D.54577D.837935D0 F400$
G64.5X-53.549Y12.1877Z-43.8034H-.085443H.019665H-.288119D.956602D.043597 F400$

```
N1Q21.00G66.32X-24.3552Y5.4685Z-43.8034H-.085443H.019665H-.996149D-.288119D.956602D.043597 T[ ] F200 [ ]$
N2G67X-24.4574Y5.8076Z-43.788H-.085193H.020711H-.996149D-.276369D.960062D.043597 L.3321 R.3772$
N3G67X-24.556Y6.1503Z-43.7724H-.084932H.021755H-.996149D-.264575D.963379D.043597 L.3343 R.3794$
N4G67X-24.6511Y6.4967Z-43.7568H-.084658H.022793H-.996149D-.25275D.966549D.043596 L.3364 R.3816$
N5G67X-24.7427Y6.8466Z-43.741H-.084371H.023829H-.996149D-.240891D.969573D.043596 L.3386 R.3839$
N6G67X-24.8305Y7.2001Z-43.7251H-.084072H.024862H-.99615D-.228993D.972451D.043597 L.3407 R.3861$
```

409

→ Retract and Approach motion between courses.

FIG. 7

SYSTEMS AND METHODS FOR USING LIGHT TO INDICATE DEFECT LOCATIONS ON A COMPOSITE STRUCTURE

FIELD

The present invention relates generally to the fabrication of composite structures with material placement machines. More particularly (but not exclusively), the present invention relates to systems and methods for using light to indicate defect locations on a composite structure, such as the locations of defects detected by an in-process vision inspection system during fabrication of the composite structure.

BACKGROUND

Composite structures have been known in the art for many years. Although composite structures can be formed in many different manners, one advantageous technique for forming composite structures is a, automated material placement process, such as an automated fiber placement or automated collation process described in U.S. patent application Ser. No. 10/068,735, filed on Feb. 6, 2002, entitled "Composite Material Collation Machine and Associated Method for High Rate Collation of Composite Materials". The contents of U.S. patent application Ser. No. 10/068,735 are incorporated herein by reference in its entirety as if fully set forth herein.

In an automated collation technique, one or more ribbons of composite material (also known as composite strands or tows) are laid down on a substrate with a material placement machine. The substrate may be a tool or mandrel, but, can also be formed of one or more underlying layers of composite material that have been previously laid down and compacted.

Fiber placement processes typically utilize a heat source to assist in compaction of the plies of composite material at a localized nip point. In particular, the ribbon or tow of composite material and the underlying substrate are heated at the nip point to increase the tack of the resin of the plies while being subjected to compressive forces to ensure adhesion to the substrate. To complete the part, additional strips of composite material can be applied in a side-by-side manner to form layers and can be subjected to localized heat and pressure during the consolidation process.

Unfortunately, defects can occur during the placement of the composite strips onto the underlying composite structure. Such defects can include tow gaps, overlaps, dropped tows, puckers (i.e., raised regions in a tow), and twists. In addition, foreign objects and debris (FOD), such as resin balls and fuzz balls, can accumulate on a surface of the composite structure which must be detected, identified and eventually removed from the ply surface.

Composite structures fabricated by automated material placement methods typically have specific maximum allowable size requirements for each flaw, with these requirements being established by the production program. Production programs also typically set well-defined accept/reject criteria for maximum allowable number of (i.e., density) of defects-per-unit area and maximum allowable cumulative defect width-per-unit area.

To ensure that the composite laminates fabricated by fiber placement processes satisfy the requirements pertaining to defect size, the structures are typically subjected to a 100% ply-by-ply visual inspection. These inspections are traditionally performed manually during which time the fiber placement machine is stopped and the process of laying materials halted until the inspection and subsequent repairs, if any, are completed. In the meantime, the fabrication process has been disadvantageously slowed by the manual inspection process and machine downtime associated therewith.

Recently, systems and methods have been developed that are capable of detecting, measuring, and marking individual defects in the composite structure. Exemplary systems and methods capable of accurately and reliably detecting, measuring and/or marking defects in a composite structure are disclosed in U.S. patent application Ser. No. 09/819,922, filed Mar. 28, 2001, entitled "System and Method for Identifying Defects in a Composite Structure"; U.S. patent application Ser. No. 10/217,805, filed Aug. 13, 2002, entitled "System for Identifying Defects in a Composite Structure"; and U.S. patent application Ser. No. 10/628,691, filed Jul. 28, 2003, entitled "Systems and Methods for Identifying Foreign Objects and Debris (FOD) and Defects During Fabrication of a Composite Structure." The entire disclosures of U.S. patent application Ser. Nos. 09/819,922, 10/217,805, and 10/628,691 are each incorporated herein by reference as if fully set forth herein.

Systems and methods have also been developed which are capable of determining a defect characteristic representative of the composite structure, such as a defect density-per-unit area and/or cumulative defect width-per-unit area. Exemplary systems and methods capable of determining defect characteristics are disclosed in U.S. patent application Ser. No. 10/726,099, filed Dec. 2, 2003, entitled "Systems and Methods for Determining Defect Characteristics of a Composite Structure", the entire contents of which are incorporated herein by reference as if fully set forth herein.

Systems and methods have also been developed which enable a material placement machine to automatically return to defects for manual defect repair, and/or that enable the machine to automatically return to and repair defects without operator intervention. Exemplary systems and methods are disclosed in U.S. patent application Ser. No. 10/799,306, filed Mar. 12, 2004, entitled "Systems and Methods Enabling Automated Return to and/or Repair of Defects with a Material Placement Machine", the entire contents of which are incorporated herein by reference as if fully set forth herein.

The above-mentioned inspection systems and methods have worked well for their intended purposes and have reduced unproductive down time associated with inspection and repair of laminate plies. The inventors hereof have recognized, however, that such systems and methods can be even further improved by providing suitable non-contact marking alternatives to ink-based surface marking systems. By way of background, ink-based marking systems can employ various means, such as inkjet marking, pump-fed felt-tip marker, spring-loaded marking pen, among others, to deposit an amount of ink onto the composite structure in those areas where defects have been detected. With these ink-based marking systems, the ink should be carefully selected to ensure compatibility with the composite substrate and to ensure that the ink doesn't contaminate the composite substrate. The ink should also be low enough in viscosity so that it flows freely through the supply lines and the sprayer nozzle. The solvents used in the ink should also allow the ink to dry quickly enough to prevent runs on the part surface, but slowly enough to eliminate clogging. Carefully selecting an ink satisfying all of the conditions can require significant amounts of time and costs.

SUMMARY

The present invention relates to systems and methods capable of using light to indicate defect locations on a composite structure, such as the locations of defects detected by an in-process vision inspection system during fabrication of the composite structure.

In a preferred implementation, a method generally includes electronically accessing positional data defining one or more defect locations on a composite structure. The method also includes automatically causing at least one light source to direct light at the composite structure to indicate the defect location(s) as defined by the positional data. Accordingly, the light allows the defect location(s) to be readily ascertained for later action, such as manual defect repair and/or FOD removal by an operator.

In another preferred implementation, a system generally includes at least one light source and a controller operatively associated with the light source. The controller is capable of electronically accessing positional data defining one or more defect locations on the composite structure. Without operator assistance, the controller can automatically cause the light source to direct light at the composite structure to indicate the defect location(s) as defined by the positional data.

In another preferred implementation, a program generally includes a computer executable module for electronically accessing positional data defining one or more defect locations on the composite structure. The program also includes a computer executable module for automatically generating instructions for automatically causing at least one light source to direct light at the composite structure to indicate the defect location(s) as defined by the positional data.

The features, functions, and advantages can be achieved independently in various embodiments of the present inventions or may be combined in yet other embodiments.

BRIEF DESCRIPTION OF THE DRAWINGS

The present invention will become more fully understood from the detailed description and the accompanying drawings, wherein:

FIG. 7 illustrates an exemplary block of NC code for generating corresponding retract and approach motions of the material placement machine between courses;

DETAILED DESCRIPTION OF THE PREFERRED EMBODIMENTS

The following description of the preferred embodiments is merely exemplary in nature and is in no way intended to limit the invention, its application, or uses.

According to one aspect, the invention provides systems and methods for using light to indicate locations of flaws and defects on a composite structure. In a preferred implementation, a method generally includes electronically accessing positional data defining one or more defect locations on a composite structure. The positional data can be extracted from a part fabrication file in which resides numerical control (NC) data that can be used by a material placement machine in fabricating the composite structure. The positional data can define one or more locations on the composite structure at which defects have been detected, such as dropped tows, tow gaps, foreign objects and debris (FOD), puckers, etc.

The method also includes automatically causing (e.g., activating, steering, light splitting, etc.) at least one light source (e.g., a laser projection device, laser pointer, etc.) to direct light at the composite structure to indicate (e.g., illuminate, highlight, circumscribe, etc.) the defect location(s) as defined by the positional data. The light allows the defect locations to be readily ascertained for later action, such as defect repair and/or FOD removal by an operator.

According to another aspect of the invention, a system generally includes at least one light source and a controller associated with the light source. The controller is capable of accessing positional data defining one or more defect locations on the composite structure. Without operator assistance, the controller can automatically cause the light source to direct light at the composite structure to indicate the defect location(s) as defined by the positional data.

Yet another aspect of the invention provides a program that generally includes a computer executable module for electronically accessing positional data defining one or more defect locations on the composite structure. The program also includes a computer executable module for automatically generating instructions for automatically causing at least one light source to direct light at the composite structure to indicate the defect location(s) as defined by the positional data.

Although aspects of the present invention can be described with a program having a direct effect on and direct control of one or more light sources, it should be understood that it is the instructions generated upon execution of the program, for example, by a processor of a control interface, and the subsequent implementation of such instructions by the processor, that have direct effect on and direct control of the light source(s).

Figure 1:
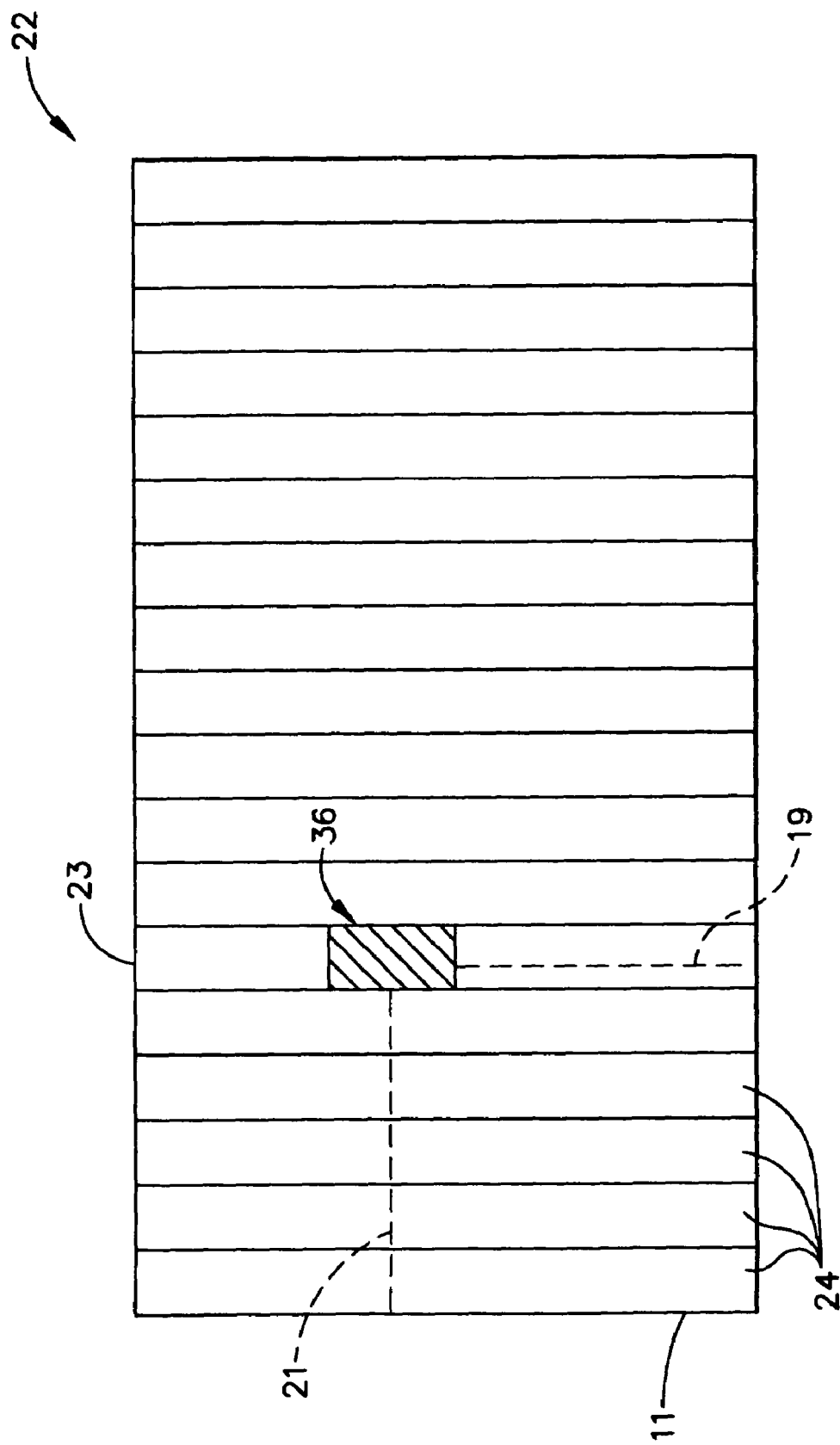
FIG. 1 is a schematic view of an exemplary composite structure illustrating linear and lateral distances to a defect in the composite structure.

FIG. 1 illustrates an exemplary composite structure 22, which can include a plurality of layers or plies. Each ply is generally comprised of a plurality of adjacent tows or strips of composite tape 24. The strips 24 typically include a plurality of fibers embedded in a resin or other material that becomes tacky or flowable upon the application of heat. The strips 24 can be arranged on a work surface, such as a table, mandrel, or other tool 26 (FIG. 8), and compacted with a compaction roller 20 (FIG. 9) to form the composite structure 22 according to an automated collation technique, such as that described in U.S. patent application Ser. No. 10/068, 735.

As shown in FIG. 1, eighteen courses or strips 24 have been completed by the material placement machine. That is, the material placement machine has made eighteen passes across a substrate. During each of the passes, the material placement machine has laid down a strip 24 on the substrate. The sixth course 23 of the composite structure 22 includes a defect 36 where a portion of a tow is missing. The dashed line 19 represents the linear distance along the sixth course 23 to the defect 36. The dashed line 21 represents the lateral distance to the defect 36 from a first end 11 of the composite structure 22.

Various implementations of the invention can be used with an inspection system capable of detecting, measuring, marking, displaying images of defects, and/or establishing and retaining generally precise defect locations, such as the exemplary systems described in U.S. patent application Ser. Nos. 09/819,922, 10/217,805, 10/628,691, 10/726,099, and/ or 10/799,306.

Upon detection of a defect, an inspection system can send a signal to trigger an ink-based marking device (e.g., inkjet marking, pump-fed felt-tip marker, spring-loaded marking pen, etc.) to place a visually prominent ink indication next to the defect. In various implementations of the present invention, the signal(s) for triggering the ink-based marking device are instead used to trigger at least one light source to direct light at the composite structure to indicate defect location(s).

Figure 15:
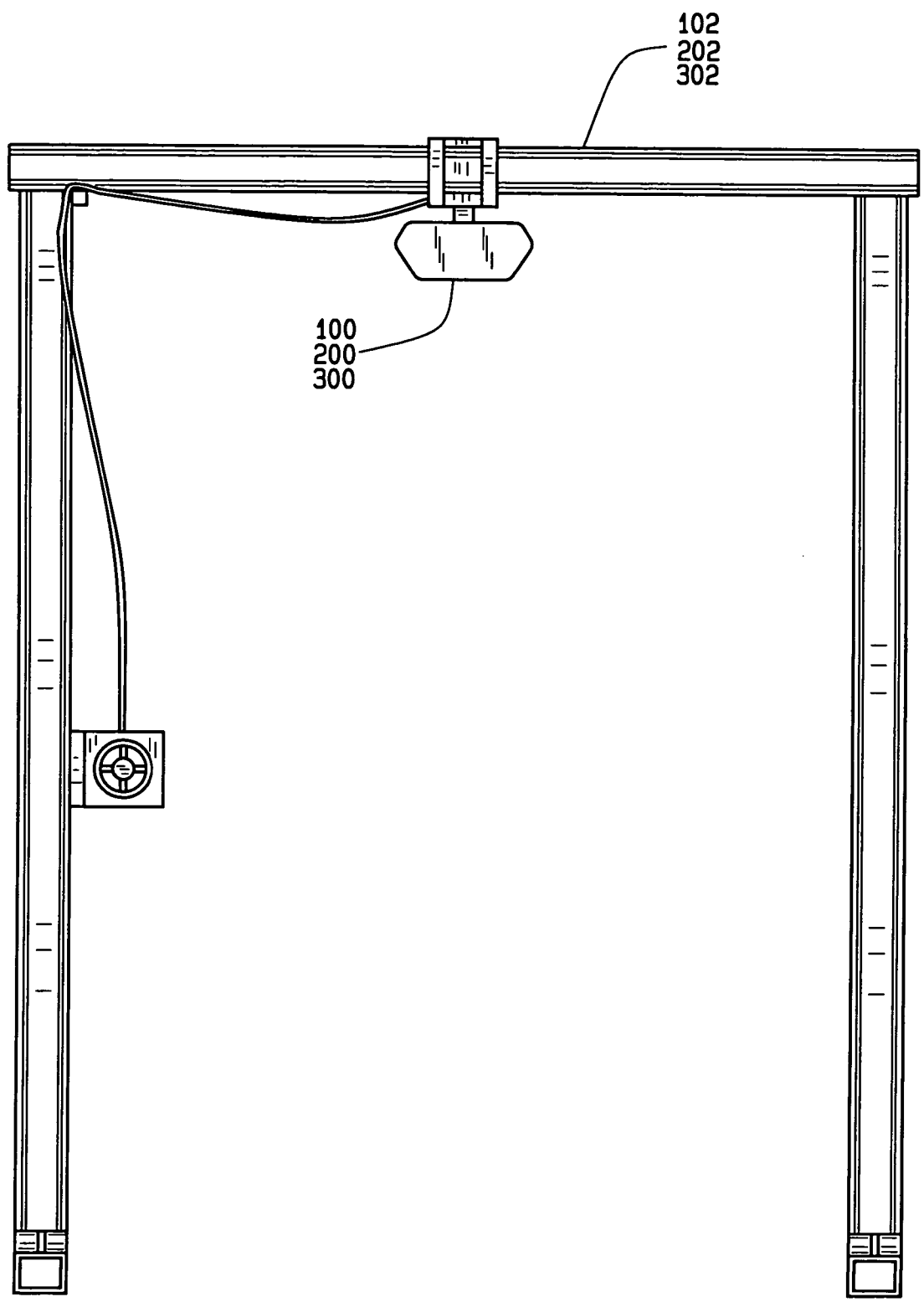
FIG. 15 is a perspective view of an exemplary gantry supporting a light source that can be used to indicate defect locations on a composite structure according to a preferred implementation.

Various implementations can include mounting the light source to a stationary location adjacent the material placement machine and the work surface (e.g., tool 26 in FIG. 8, etc.) on which the composite structure is being fabricated. By way of example, FIG. 15 illustrates a light source 100, 200, 300 being supported by a framework or gantry 102, 202, 302, which can be independent or separate from the material placement machine. Alternatively, the light source can be mounted directly to a stationary portion of the material placement machine. Stationary mounting of the light source enables the light source to be positioned and calibrated relative to a specific reference point on the work surface on which the composite structure is being fabricated.

Figure 3:
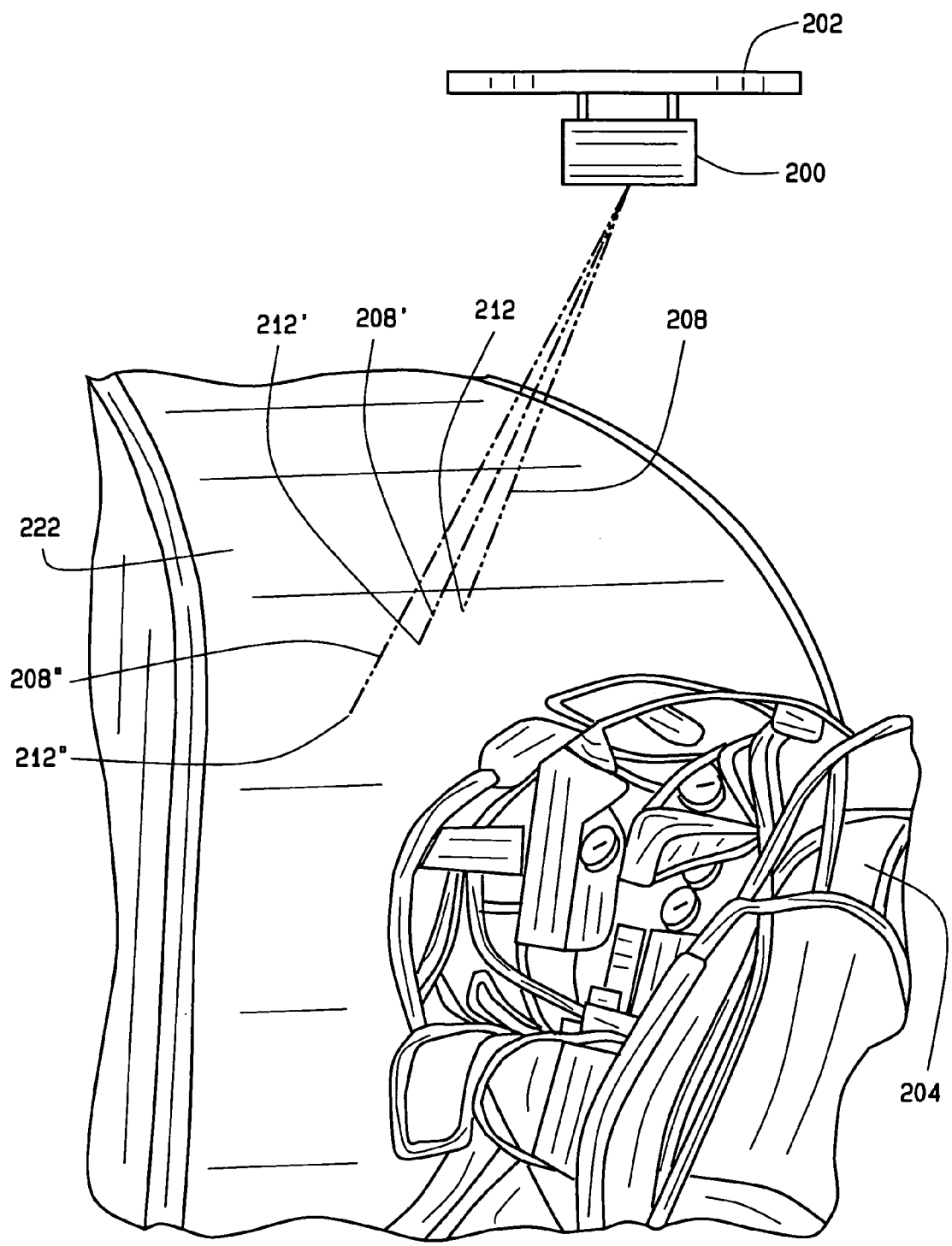
FIG. 3 is a perspective view of a light source indicating several defect locations on a composite structure according to another preferred embodiment on the invention.
Figure 4:
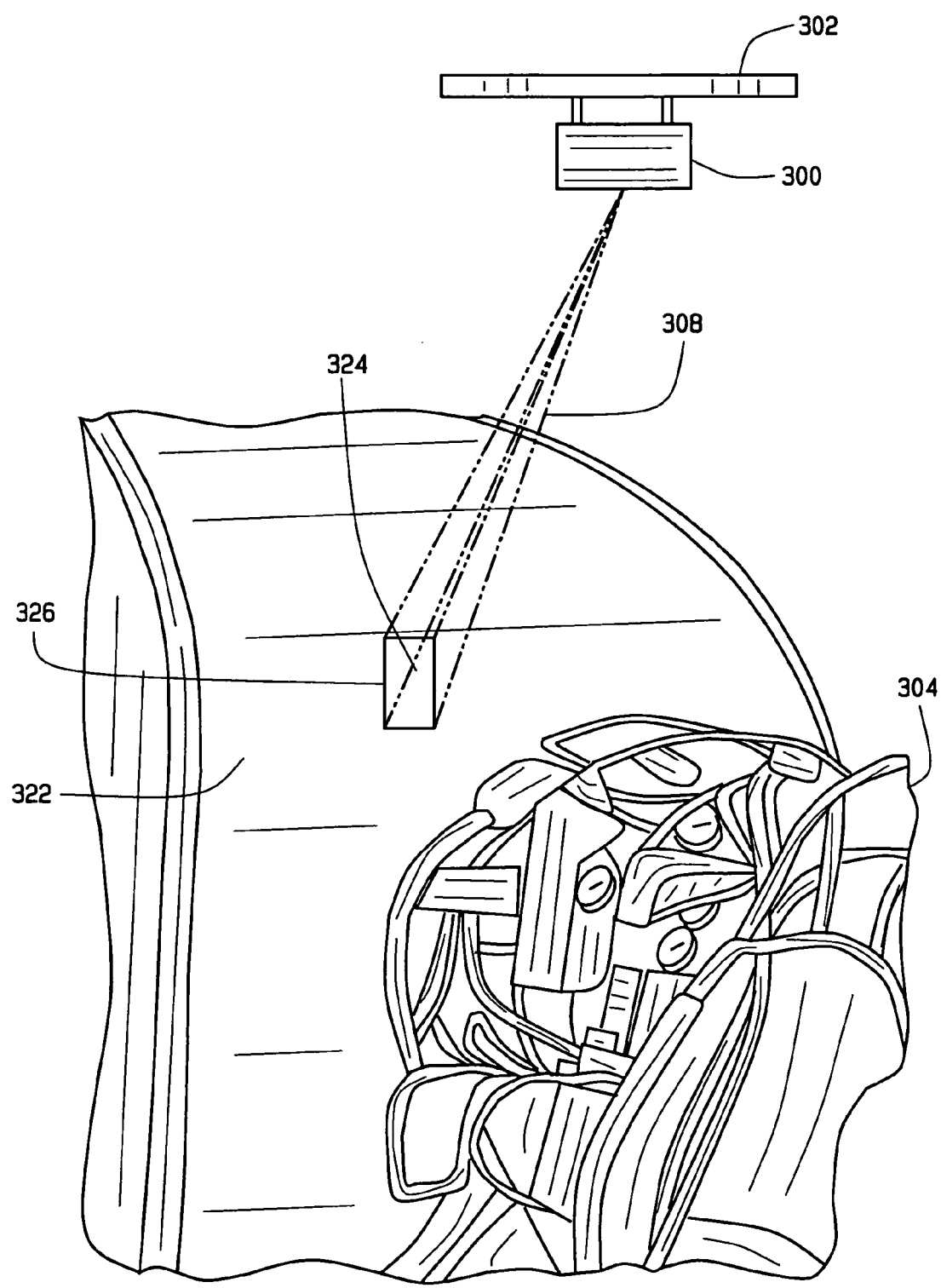
FIG. 4 is a perspective view of a light source indicating a region of a composite structure which includes one or more defect locations according to another preferred embodiment on the invention.

As described below, the light source can be adapted to project a single point (FIG. 2), multiple points (FIG. 3), or what appears to be a continuous line forming a boundary or template (e.g., box, circle, triangle, etc.) on the composite structure (FIG. 4). Locations to which the light is projected can be derived from coordinates taken from a computer-aided drawing (CAD) file. This CAD file can be created using various commercially available software programs. In an exemplary application, coordinates can be repetitive for the same part, assembly, or laminate.

Positional or coordinate information defining defect locations will change continuously based on the particular locations of the detected flaws. Exemplary systems and methods for determining a location of a defect on the laminate can include tracking course number and distance along a course by encoded positioning as described in U.S. patent application Ser. No. 10/726,099.

Upon detection of a flaw, a computer associated with the inspection system can signal a computer associated with the material placement machine to extract coordinate data from an appropriate numerical control (NC) block of the material placement program. This process is described generally below and in more detail in U.S. patent application Ser. No. 10/799,306. Extracted coordinate data can be maintained or stored to allow subsequent access thereto. For example, extracted coordinate data can be stored at least until placement of the current ply is complete and/or disposition (e.g., defect repair, FOD removal, etc.) activities begin.

A control interface can be used to control and manage the transfer of coordinate data. The control interface can also control and manage the light source (e.g., activate, steer, etc.). In various implementations, coordinates can be converted to CAD format prior to their transfer to the control interface and use in steering the light source.

Figure 2:
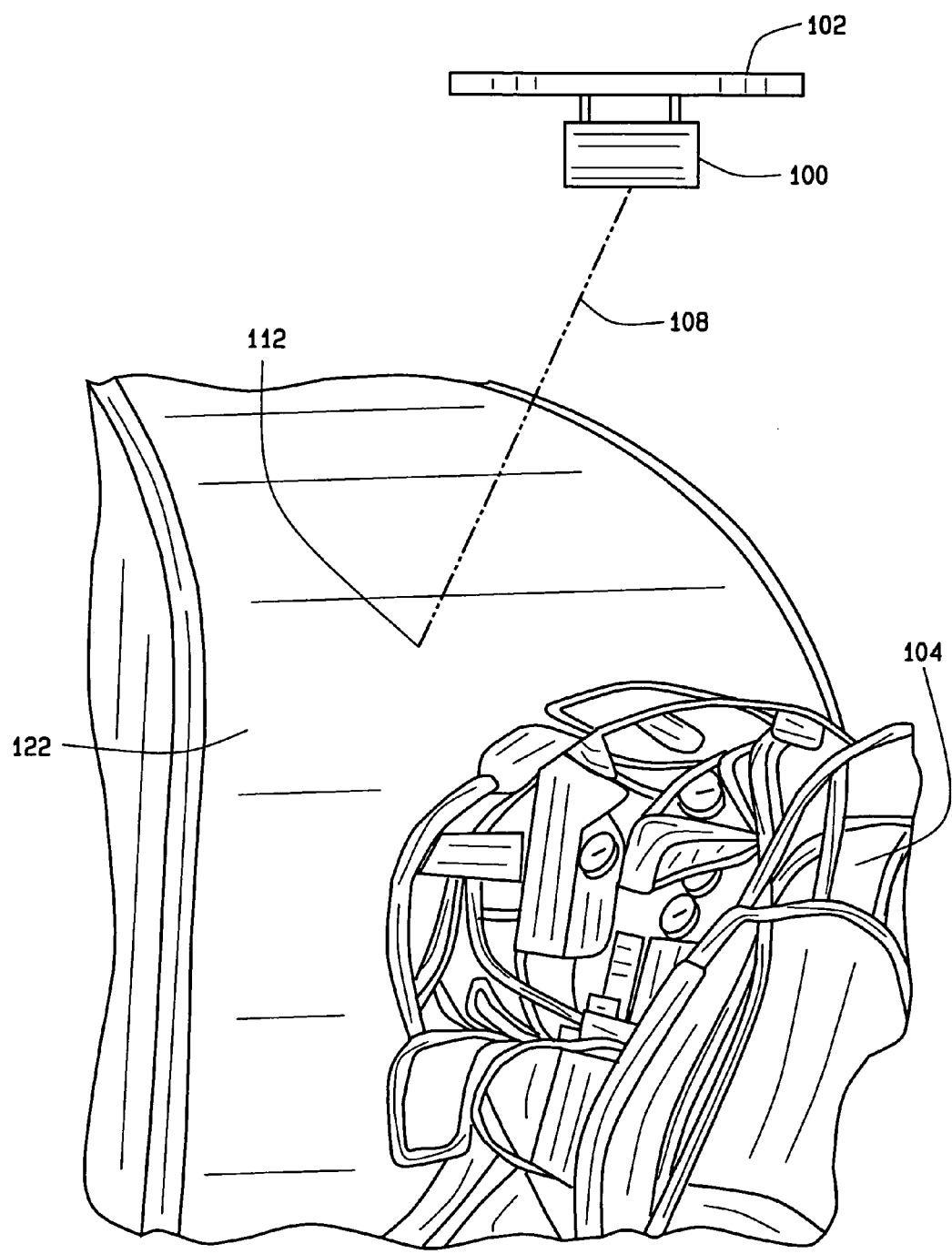
FIG. 2 is a perspective view of a light source indicating a defect location on a composite structure according to a preferred embodiment of the invention.

The actual marking or illumination by a light source to indicate defect locations on the laminate can be accomplished in several ways such as the exemplary approaches shown in FIGS. 2 through 4. It should be noted, however, that FIGS. 2 through 4 are for purposes of illustration only and not for purposes of limitation. For example, FIGS. 2 through 4 each illustrate a laser projection device 100, 200 and 300 being used to indicate one or more defect locations on a composite structure. But other implementations can include using any number of (i.e., one or more) light sources selected from a wide range of other suitable light source types besides laser.

FIG. 2 illustrates a laser pointer or projection device 100 coupled to a stationary framework or gantry 102 at a position above and adjacent a robotic head unit 104 of a material placement machine. Alternatively, other mounting arrangements are possible for the laser projection device 100. For example, the laser projection device 100 can instead be mounted directly to a stationary portion of the material placement machine.

As shown, the laser projection device 100 is directing light 108 at a defect location 112 on the composite structure 122, thereby illuminating the defect location 112 and making it readily visible to an operator. Again, however, other suitable light sources besides laser can also be employed.

FIG. 2 generally represents a single sequential marking approach in which defect coordinates are transferred in some predetermined order. Defect locations can then be illuminated in a generally sequential fashion consistent with the transfer order such that only a single defect location is illuminated at any given time.

Each defect location can remain illuminated until disposition (e.g., defect repair, FOD removal, etc.) is completed and the next set of coordinates is transferred. In response to the new coordinates, a controller can reposition or steer the laser projection device 100 such that the light therefrom no longer illuminates the location of the repaired defect, but instead illuminates the next defect location as defined by the new coordinates.

In various implementations, an operator may manually repair the defect and/or remove FOD at the defect location being illuminated. The operator may interface or communicate with the controller to indicate the completion of the manual operation. In response thereto, the controller may then extract the next set of coordinates for the next defect location and cause the light source to illuminate that next defect location as defined by the extracted coordinates.

In other implementations, however, defects can be repaired automatically by the material placement machine without requiring manual repair or user intervention. In such implementations, a computer of the material placement machine can send an appropriate signal to the controller of the light source indicating completion of the repair. Exemplary systems and methods for enabling automated repair of defects with a material placement machine are described in U.S. patent application Ser. No. 10/799,306.

FIG. 3 illustrates a laser pointer or projection device 200 coupled to a stationary framework or gantry 202 at a position above and adjacent a robotic head unit 204 of a material placement machine. Alternatively, other mounting arrangements are possible for the laser projection device 200. For example, the laser projection device 200 can instead be mounted directly to a stationary portion of the material placement machine.

As shown, the laser projection device 200 is directing light 208, 208', and 208" at a composite structure 222 to simultaneous illuminate three defect locations 212, 212', and 212" as defined by multiple coordinate sets. Other quantities (i.e., one or more) of defect locations can also be illuminated at a given time depending on the particular application. And, one or more other suitable light sources besides laser can also be employed.

In a preferred embodiment, the laser projection device 200 can be equipped with a splitter. The splitter causes light from the laser projection device 200 to split and illuminate different defect locations on the composite structure. As an alternative to splitting the light, various implementations can also include a plurality of light sources each capable of emitting light to indicate at least one different defect location on the composite structure.

In various implementations, the laser projection device 200 can be configured to illuminate defect locations only within a certain region or particularly sized area of the composite structure 222. Alternatively, the laser projection device 200 can instead be configured to illuminate defect locations over the entire laminate.

The laser projection device 200 can continue to illuminate defect locations until repairs are completed at each defect location being illuminated. Alternatively, coordinate information can be continuously updated such that a defect location is no longer illuminated after the defect has been repaired or otherwise disposed of. In such implementations, incomplete repairs and defects needing attention can be easily determined by simply noting which defect locations remain illuminated.

FIG. 4 illustrates a laser pointer or projection device 300 coupled to a stationary framework or gantry 302 at a position above and adjacent a robotic head unit 304 of a material placement machine. Alternatively, other mounting arrangements are possible for the laser projection device 300. For example, the laser projection device 300 can instead be mounted directly to a stationary portion of the material placement machine.

As shown, the laser projection device 300 is indicating a specific area or region 324 of a composite structure 322 that includes one or more defect locations. Light 308 from the laser projection device 300 appears to be a generally continuous line defining a box 326 on the composite structure 322. Alternatively, the laser projection device 300 can be configured to project light so as to form other suitable geometric shapes or outlines (e.g., circles, triangles, among others) on the composite structure 322.

Depending on the particular application, the light source can direct light at the composite structure to indicate the defect location(s) only after the ply having the defect location(s) is completed. Alternatively, the light source can instead direct light at the composite structure as defects are being detected during the fabrication of the composite structure. In either case, updated coordinates can be utilized as each new ply is being laid by the material placement machine.

In addition, a history file can be set up to record information such as defect rejections, defect location coordinates, and repair status. The history file can reside, for example, within software associated with the inspection system, software associated with the material placement machine, a combination thereof, etc.

Optionally, various implementations of the invention can include illuminating defect locations so as to indicate and distinguish among the locations of different types of defects. For example, an exemplary implementation can include using different types of light (e.g., light differing in color, intensity, hue, saturation, brightness, different lighted patterns, different lighted shapes or symbols, combinations thereof, among other attributes) to indicate and distinguish among the locations of different types of defects. By way of example only, blue-colored light can be used to indicate a location of foreign objects and debris (FOD) on the composite structure, while red-colored light is used to indicate a location of a dropped tow or tow gap. As another example, different colors of light can be used to indicate and distinguish between unacceptable defects and acceptable defects.

Various implementations of the invention can optionally include using light to not only indicate defect locations, but also denote the category of acceptance criteria in which a defect falls. For example, an exemplary implementation can include having light form one or more indicia, patterns, alphanumeric characters, symbols, colors, combinations thereof, etc. on the composite so as to indicate and distinguish among one or more categories of acceptance criteria for defects. By way of background, a production program can specify for a part one or more different categories of acceptance criteria (e.g., maximum allowable number of defects-per-unit area, maximum allowable cumulative defect width-per-unit area, maximum allowable width of a single defect). For example, a first part region can be assigned category B which is more lenient than category A assigned to a second part region. The acceptance criteria within a category can be used for determining acceptability of a defect within a region to which that category has been assigned.

By way of example only, an exemplary implementation can include having light form a letter "A" at or near a defect within a region of the part assigned category A acceptance criteria and/or to form a letter "B" at or near a defect within another region of the part assigned category B, and so on. Using light to indicate and distinguish between categories of acceptance criteria enables the particular category of acceptance criteria for a defect to be readily ascertained by an operator or other persons.

Figure 5A:
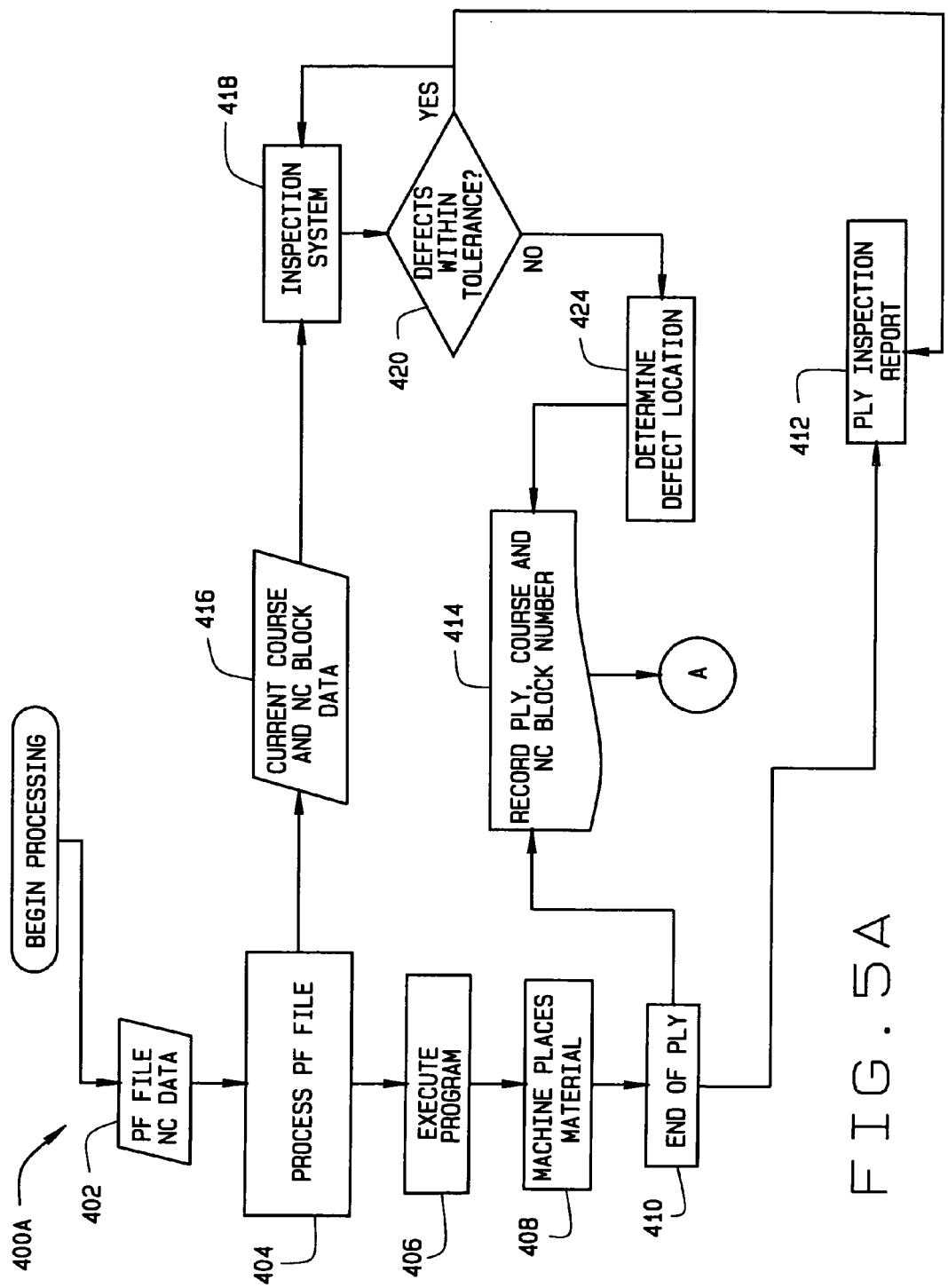
FIGS. 5A and 5B form a process flow diagram illustrating operations of a method for using light to indicate defect locations on a composite structure according to a preferred implementation.
Figure 5B:
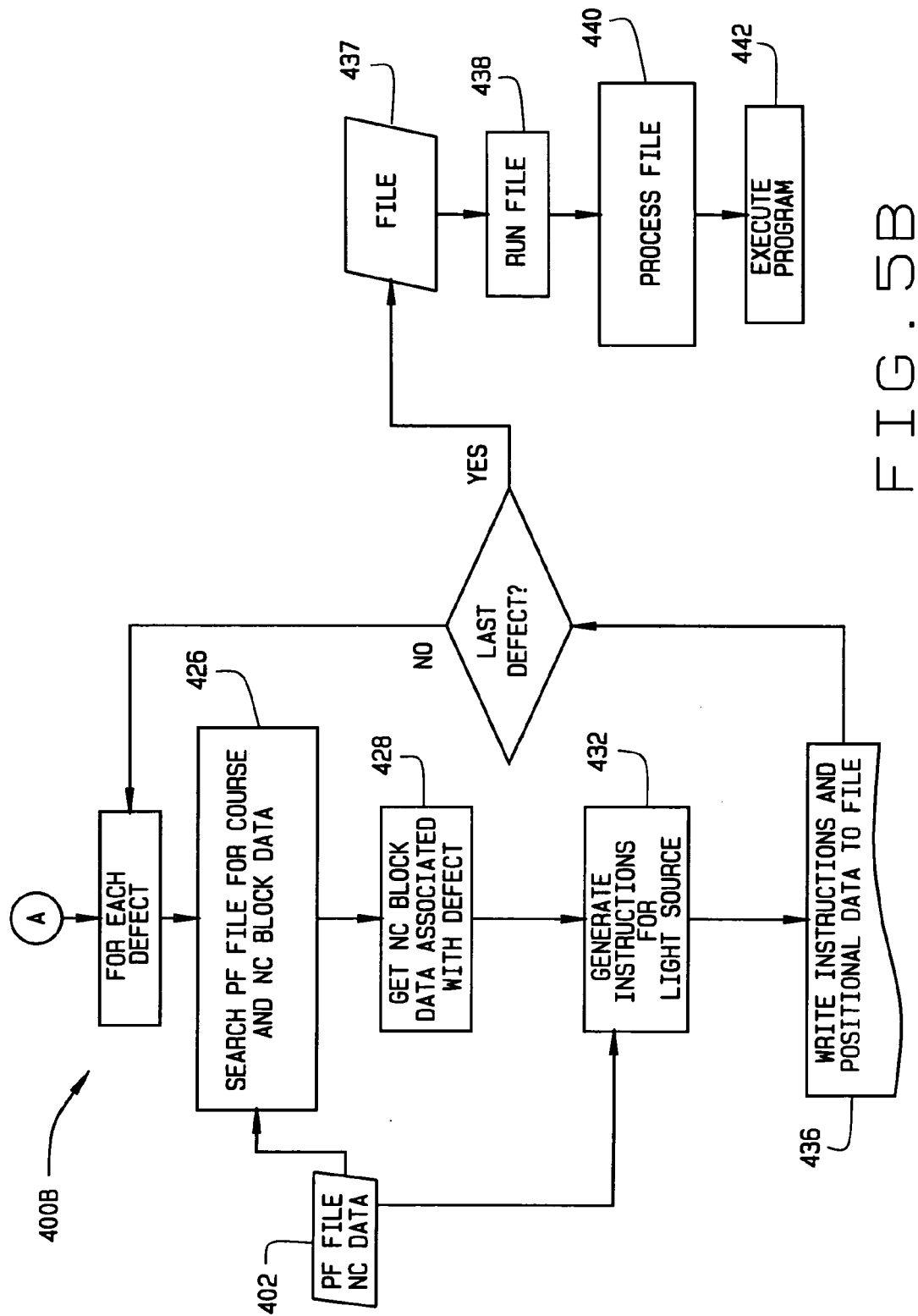

FIGS. 5A and 5B form a process flow diagram illustrating an exemplary method 400 for using light to indicate defect locations on a composite structure. As shown in FIG. 5A, the method can include intelligent front end (IFE) processing of a part fabrication file 402 at operation 404. The part fabrication file 402 can include data and information for a material placement machine to fabricate the composite structure from start to finish. Exemplary information within the file 402 can include numerical control (NC) data defining various approach and retract motions for the material placement machine and information defining part specifications, such as perimeter, size, contour, etc.

Figure 6:
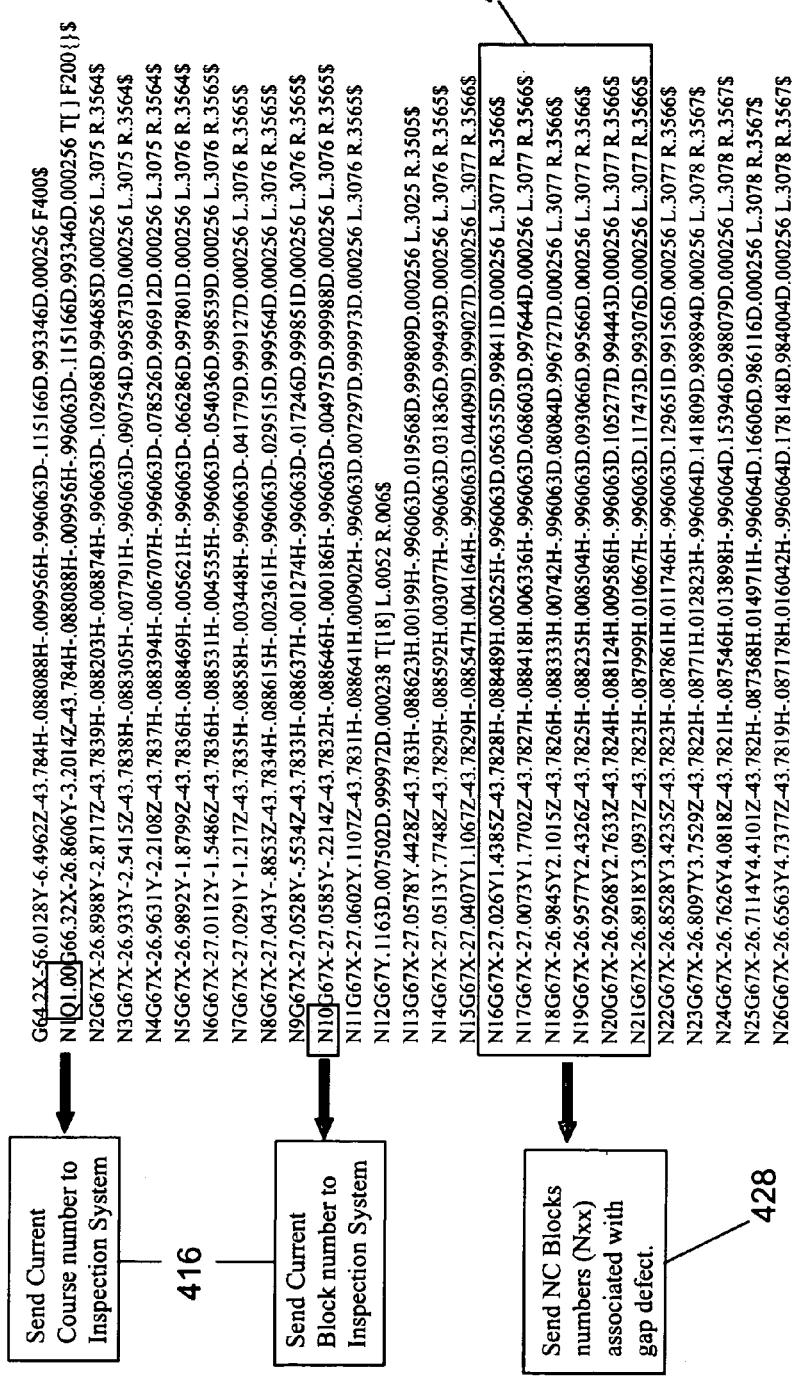
FIG. 6 illustrates an exemplary block of numerical control (NC) data within a part fabrication file for a material placement machine.

FIG. 6 illustrates an exemplary block of numerical control (NC) data 403 that may be included within a part fabrication file 402 for a particular type of material placement machine. FIG. 6 illustrates various lines of data reflecting the material placement machine's location and its operation at a specific point and time. FIG. 6 also illustrates a block 405 of lines associated with a defect location. FIG. 6 is for purposes of illustration only, and the type and content of program code for the material placement machine can vary depending on the particular application and particular material placement machine being used.

In FIG. 5A, operation 406 includes execution of a program, for example by a processor in communication with the material placement machine. Execution of the program generates instructions or commands for causing the material placement machine to begin placing the material at operation 408. FIG. 7 illustrates an exemplary block of code 409 for generating corresponding retract and approach motions of the material placement machine between courses. FIG. 7 is for purposes of illustration only, and the type and content of the program code for a material placement machine can vary depending on the particular application and particular material placement machine being used.

As shown in FIG. 5A, a ply inspection report is created at operation 412 when the material placement machine completes or comes to the end of a ply or layer, as represented by box 410. The ply, the course, and NC block number associated therewith can be logged or recorded at operation 414.

With reference to FIGS. 5A and 6, current course number and current block number 416 can be sent to an inspection system. Operation 418 (FIG. 5A) includes the inspection system inspecting the composite structure for defects. Preferably, this inspection occurs generally concurrently with operation 408 in which the material is being placed by the material placement machine. Exemplary systems and methods capable of detecting defects in a composite structure are described generally below and in more detail in U.S. patent application Ser. Nos. 09/819,922, 10/217,805, 10/628,691, 10/726,099, and/or 10/799,306.

Operation 420 includes determining whether a detected defect is acceptably within certain predefined tolerances or criteria, such as maximum allowable dimensional parameters and tolerances as established by production program. By way of example only, this determination can be made by counting the number of pixels from a digital image representing the defect and then using that pixel count to compute an indirect quantitative measurement for the defect based upon correlation data including a predetermined relationship between pixel count and distance or dimensional limits.

Alternative implementations can also include an operation for determining whether a defect (e.g., a defect determined to be unacceptable at operation 420) can be repaired automatically by the material placement machine without requiring manual repair or user intervention. Exemplary defect types that can be repaired by automation are dropped tows and tow gaps having a width equal to the width of a tow. Information about defects that are determined to be irreparable by automation can be logged or recorded in the ply inspection report at operation 412. Exemplary defect types which may be determined to be incapable of being repaired by automation with the material placement machine can include foreign objects and debris (FOD) and unacceptable/rejected gaps that are narrower than the width of a tow.

Operation 424 includes determining a location for each defect determined to be unacceptable at operation 420. In alternative implementations, operation 424 can include determining a location for each and every defect detected by the inspection system (operation 418). In other implementations, operation 424 can include determining a location for each defect detected by the inspection system (operation 418) determined to be unacceptable (operation 420) and also determined to be incapable of being repaired by automation. In yet other implementations, operation 424 can include determining a location for each defect detected by the inspection system (operation 418) and determined to be irreparable by automation regardless of whether the defect is determined to be acceptable or unacceptable.

In preferred implementations, defect locations can be determined by exterior monitoring of the material application/lay-down position of the material placement machine. Exemplary systems and methods capable of establishing and retaining generally precise defect locations on the laminate are described generally below and in more detail in U.S. patent application Ser. No. 10/726,099.

The positional data defining defect locations or coordinates can be logged, recorded and tracked at operation 414.

With reference now to FIGS. 5B and 6, operation 426 includes searching the part fabrication file 402 (FIG. 5B) for course and NC block data 405 (FIG. 6) associated with a defect. By way of example, the inspection system upon detection of defect can produce a signal which is used to flag or identify the numerical control block data defining the coordinates for that defect's location.

At operation 428, the NC block data 405 associated with the defect is obtained or extracted.

Operation 432 includes creating instructions or commands for the light source. Creating these instructions can include accessing the part fabrication file 402. These instructions can automatically cause (e.g., activate, steer, etc.) the light source to direct light at the composite structure to highlight or indicate the location at which a defect is located. Preferably, these instructions for the light source are automatically written based on NC block information and data from the inspection/vision system.

At operation 436, the instructions and positional data (e.g., NC block data 405 extracted at operation 428, commands created at operation 432) can be written to a file 437.

Operations 426 through 436 can be repeated for each defect detected by the inspection system (operation 418, FIG. 5A) determined to be unacceptable (operation 420).

Operation 438 can include running the file 437. Operation 440 can include intelligent front end (IFE) processing of the file 437.

Operation 442 includes execution of the program to cause the light source to direct light at the composite structure to indicate defect locations on the composite structure. This can be accomplished in various ways and with various types of light sources. Exemplary approaches are described above and shown in FIGS. 2 through 4.

Alternative implementations can include using light to indicate each and every defect detected by the inspection system (operation 418, FIG. 5A) in which case operation 420 can be eliminated. Operation 424 can include determining a location for each and every defect detected by the inspection system at operation 418. Operations 426 through 436 can be repeated for each defect detected by the system at operation 418.

Yet other implementations can include using light to indicate only those defects determined to be unacceptable (operation 420) and also determined to be incapable of being repaired by automation. This latter determination can be made, for example, at an operation between operations 420 and 424. Operation 424 can include determining a location for only those defects detected by the inspection system (operation 418, FIG. 5A) determined to be unacceptable (operation 420) and also determined to be incapable of being repaired by automation. The number of times that operations 426 through 436 are repeated will depend on the number of such defects.

Still yet other implementations can include using light to highlight defects detected by the inspection system (operation 418, FIG. 5A) and determined to be incapable of being repaired by automation without regard for whether such defects are determined to be unacceptable. Operation 420 can include determining whether a detected defect is repairable by automation. Operation 424 can include determining a location for each defect detected by the inspection system (operation 418, FIG. 5A) and determined to be irreparable by automation. The number of times that operations 426 through 436 are repeated will depend on the number of such defects.

In each of these various implementations, method 400 enables automated generation of program code for automatically causing one or more light sources to direct light at a composite structure to indicate defect locations on the composite structure.

Accordingly, implementations of the invention utilize light to make defect locations on a composite structure readily identifiable by an operator. This usage of light to indicate defect locations eliminates the need to apply foreign material (e.g., ink, other marking media, etc.) onto the ply surface, and also enables further reductions in machine down time by eliminating the required maintenance associated with ink-based marking systems to keep ink lines clear, reservoirs filled, and tips primed.

In addition, light-based marking systems can be less complex and more compact than ink-based marking systems wherein one or more suitable light sources can replace numerous ink-based marking components, such as relatively complex hardware, attachment hardware, pumps, reservoirs, solenoids, and applicators.

Using light instead of ink to indicate defect locations also eliminates any concerns about surface contamination of the laminate by the ink (or other marking media) and any potential of such contamination to reduce structural performance of the part. Providing a suitable alternative to ink-based marking systems also eliminates the cost and time normally required to carefully select an appropriate ink that is compatible (won't act as a contaminant) with the composite substrate, has a low enough viscosity to freely flow through supply lines and nozzles, and dries quickly enough to prevent runs on the part surface but dries slowly enough to eliminate clogging.

Figure 8:
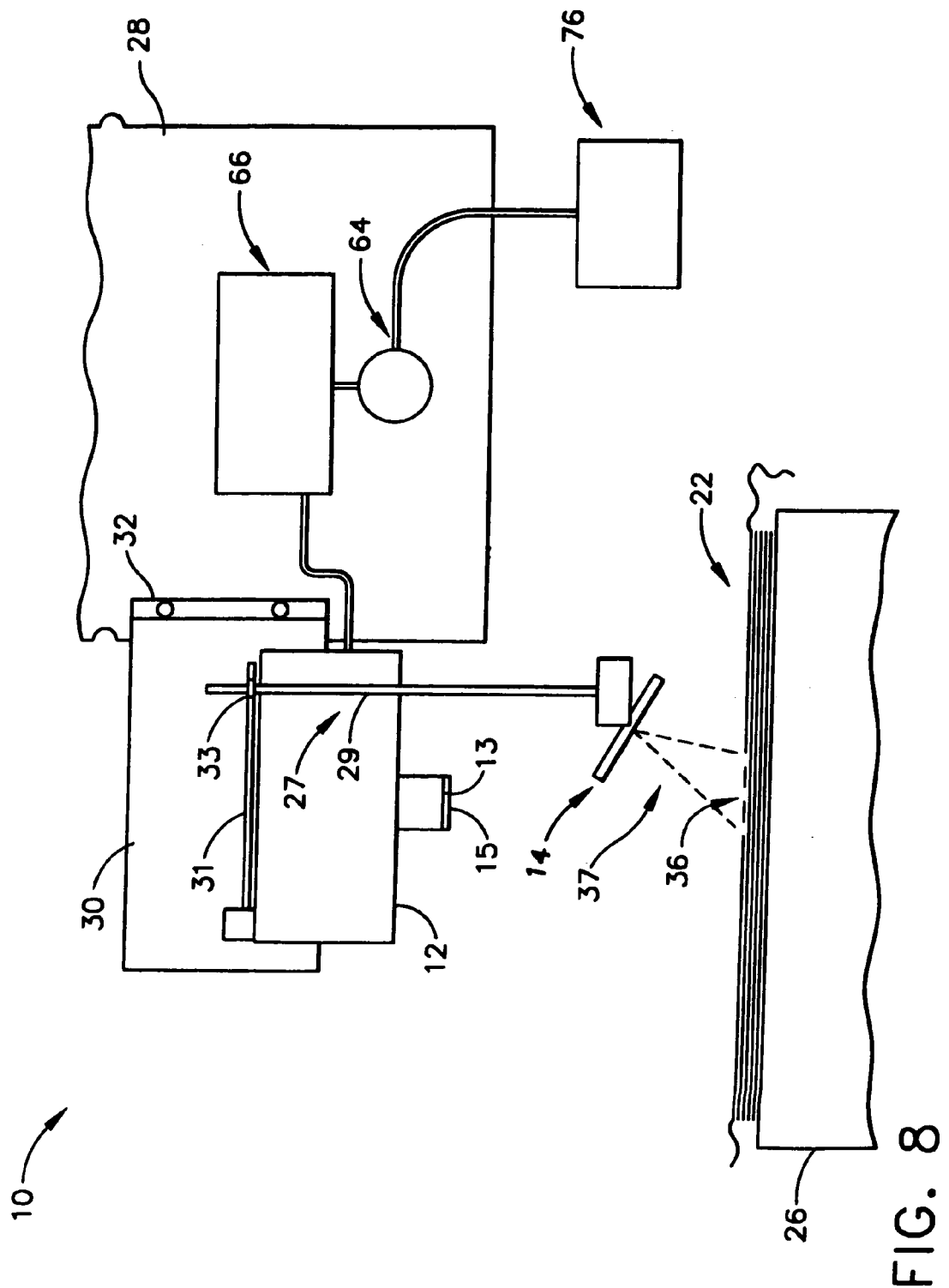
FIG. 8 is a schematic view of an exemplary system for using light to indicate defect locations positioned adjacent an exemplary system for inspecting a composite structure for defects.
Figure 9:
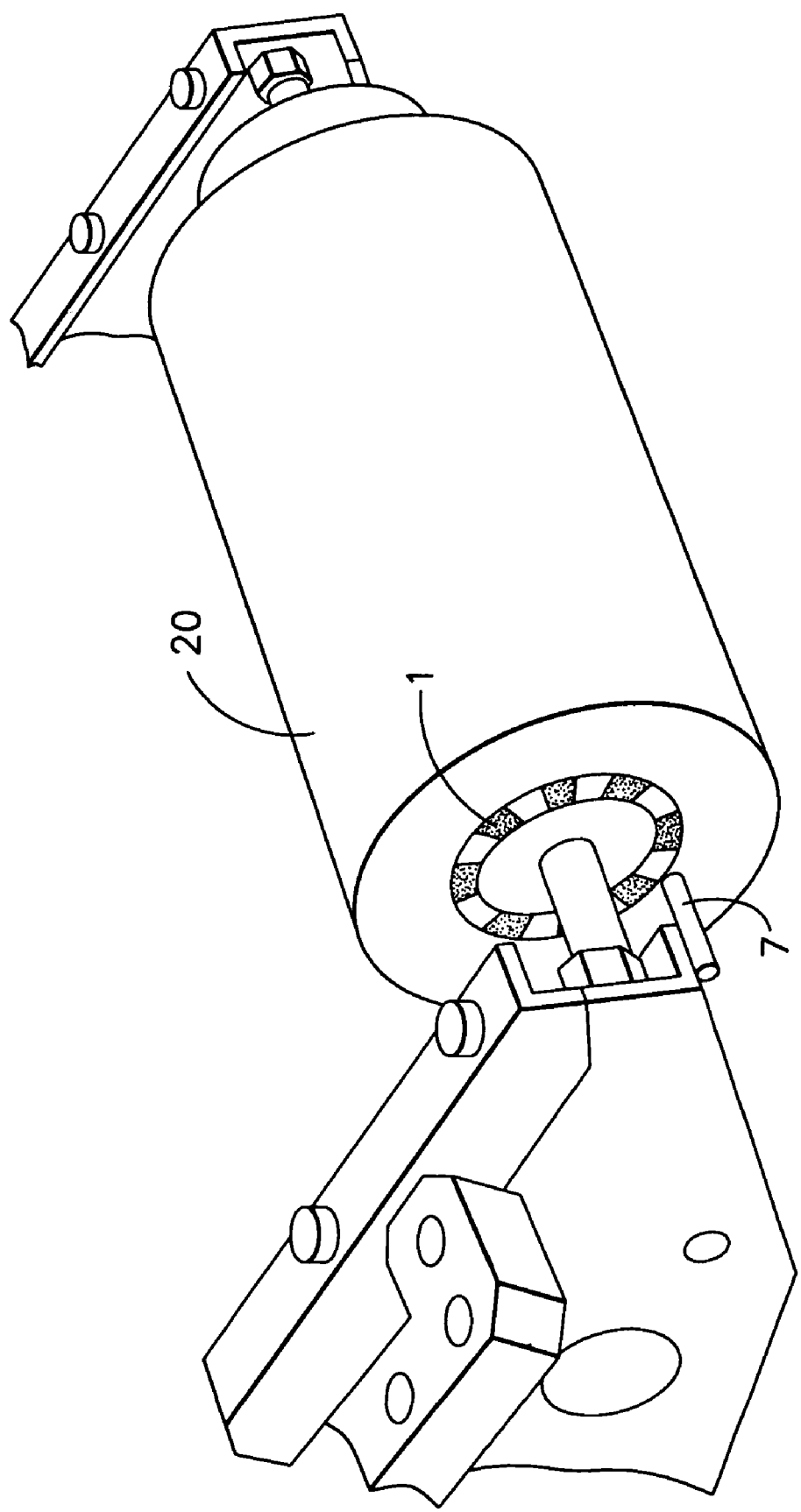
FIG. 9 is a perspective view of an exemplary compaction roller having a code ring coupled thereto for common rotation therewith and a photo sensor positioned to monitor the code ring.

An exemplary system 10 which can be used at operation 416 (FIG. 5A) to detect defects in a composite structure is illustrated in FIG. 8. It is understood that while various implementations are described herein in conjunction with the system 10, various implementations of the invention can also be used with other inspection systems. The following description of the system 10 is merely exemplary in nature and is in no way intended to limit the various implementations of the invention, their applications and/or uses.

As shown in FIG. 8, the system 10 includes at least one camera 12 and at least one light source 14. The camera 12 is connected to a processor 66 for interpreting the images the camera 12 captures, or to a storage device 64 for storing the images, or both, as discussed more fully below.

The system 10 may also include a user interface 76 that is in communication with the processor 66. The user interface can be programmed such that it can run from a wide range of software applications, including but not limited to DOS, Windows 98, Windows/NT, Windows 2000, Windows CE, Linux, Unix, and equivalents. The user interface 76 can include a display screen, such as on a computer monitor, and can also include an input device, such as a keyboard and mouse (not shown), for permitting an operator to move a cursor about the display screen and input various system settings and parameters. The display screen can also be touch-sensitive for permitting the operator to input the desired settings by manually touching regions of the display screen. The user interface 76 can includes a window in which an image of the composite structure is displayed for viewing by an operator or other user.

The light source 14 is positioned to emit light for illuminating the composite structure 22. The illumination is reflected differently by defects in the composite structure than from portions of the composite structure that are defect free. For example, illumination reflecting off non-defective portions of the composite structure 22, and light that fails to reflect off of defects in the composite structure 22, or vice versa, creates visible images that can be captured by the camera 12. Details regarding systems and methods for identifying defects in a composite structure during fabrication thereof are included in previously referred to U.S. patent application Ser. Nos. 09/819,922, 10/217,805, 10/628,691, 10/726,099, and 10/799,306.

Figure 10:
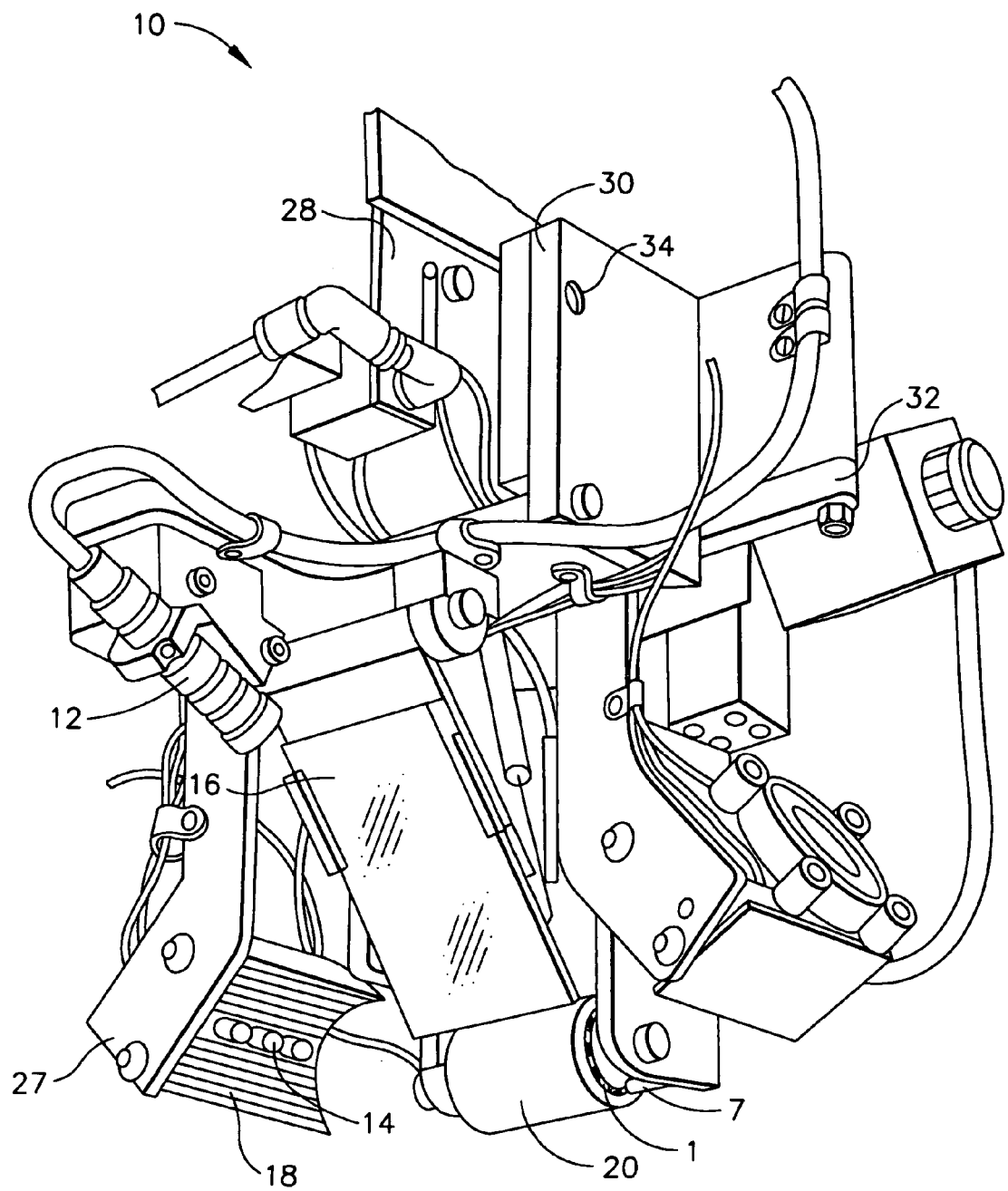
FIG. 10 is a perspective view of another exemplary system for inspecting a composite structure for defects.

As shown in FIG. 8, the camera 12 is positioned near the composite structure 22 so as to capture images of portion of the composite structure being illuminated, which is typically immediately downstream of the nip point at which a composite tow is joined with the underlying structure. Alternatively, and as shown in FIG. 10, a reflective surface 16 may be positioned near the composite structure (the composite structure is not shown in FIG. 10), and angled such that the reflective surface 16 reflects an image of the illuminated portion of the composite structure. The camera 12 may be positioned to point toward the reflective surface 16 in order to capture close-range images of the illuminated portion of the composite structure from the reflective surface 16. More than one reflective surface 16 may also be utilized in further embodiments of the invention in which the reflective surfaces 16 cooperate in order to direct images of the illuminated portion of the composite structure to the camera 12.

A wide range of cameras can be used including commercially-available cameras capable of acquiring black and white images. In one embodiment, the camera 12 is a television or other type of video camera having an image sensor (not shown) and a lens 13 (FIG. 8) through which light passes when the camera 12 is in operation. Other types of cameras or image sensors can also be used, such as an infrared-sensitive camera, a visible light camera with infrared-pass filtration, a fiber optic camera, a coaxial camera, Charge Coupled Device (CCD), or Complementary Metal Oxide Sensor (CMOS). The camera 12 can be positioned proximate the composite structure 22 on a stand (not shown) or mounted to a frame 28 or similar device.

In those embodiments that do not include a reflective surface 16, the camera 12 may be mounted to the frame 28 by way of a bracket 30 and associated connectors 32, as shown in FIG. 8. The connectors 32 may be rivets, screws or the like that mount the camera 12 to the frame 28 in a stationary position. Alternatively, the connectors 32 may be a hinge-type connector that permits the camera 12, light source 14, and associated assembly to be rotated away from the composite structure 22. This embodiment is advantageous in situations where other parts of the material placement device, particularly the parts located behind the camera 12 and associated assembly, must be accessed, such as for maintenance, cleaning, or the like.

FIG. 10 illustrates an alternative embodiment of the hinge-type connector 32 that mounts the camera 12, reflective surface 16, light source 14, and associated assembly (e.g., camera assembly) to the frame 28 by way of a bracket 30. A suitable fastener, such as a thumbscrew or any other fastener that may be removed or loosened with relative ease, can be inserted through hole 34 and then tightened to secure the camera assembly in place for operation. The fastener may be loosened or removed, for example, to rotate the camera assembly away from the compaction roller 20 and other parts of the fiber placement device.

With further reference to FIG. 8, a filter 15 can be placed on the lens 13 for filtering light in a particular manner. In one embodiment, the filter 15 is designed to filter light such that only the infrared component or a certain infrared wavelength or range of wavelengths of light can pass into the camera 12. In this manner, the filter 15 prevents ambient visible light from entering the camera 12 and altering the appearance of the captured image.

Other methods of filtering light can also be used to achieve the same, or at least similar, result. For example, the camera may be designed to include a built-in filter of equivalent optical characteristics. In addition, the filter can be located between the camera lens 13 and image sensor. Alternatively, the camera may include an image sensor that is only sensitive in the infrared spectrum (e.g., an infrared-sensitive camera), thus eliminating the need for the filter.

The light source 14 of the system 10 will now be described in more detail. The light source 14 is positioned to emit light for illuminating at least a portion of the composite structure 22.

In FIG. 8, the light source 14 is shown positioned at an oblique angle 37 relative to the composite structure 22. The oblique angle 37 may be about forty-five degrees, although other angles are possible depending on the application. In addition, the light source 14 is also shown positioned to emit light in a direction substantially perpendicular to the direction of placement of the strips 24 in order to highlight the defects 36, as described below.

Figure 12:
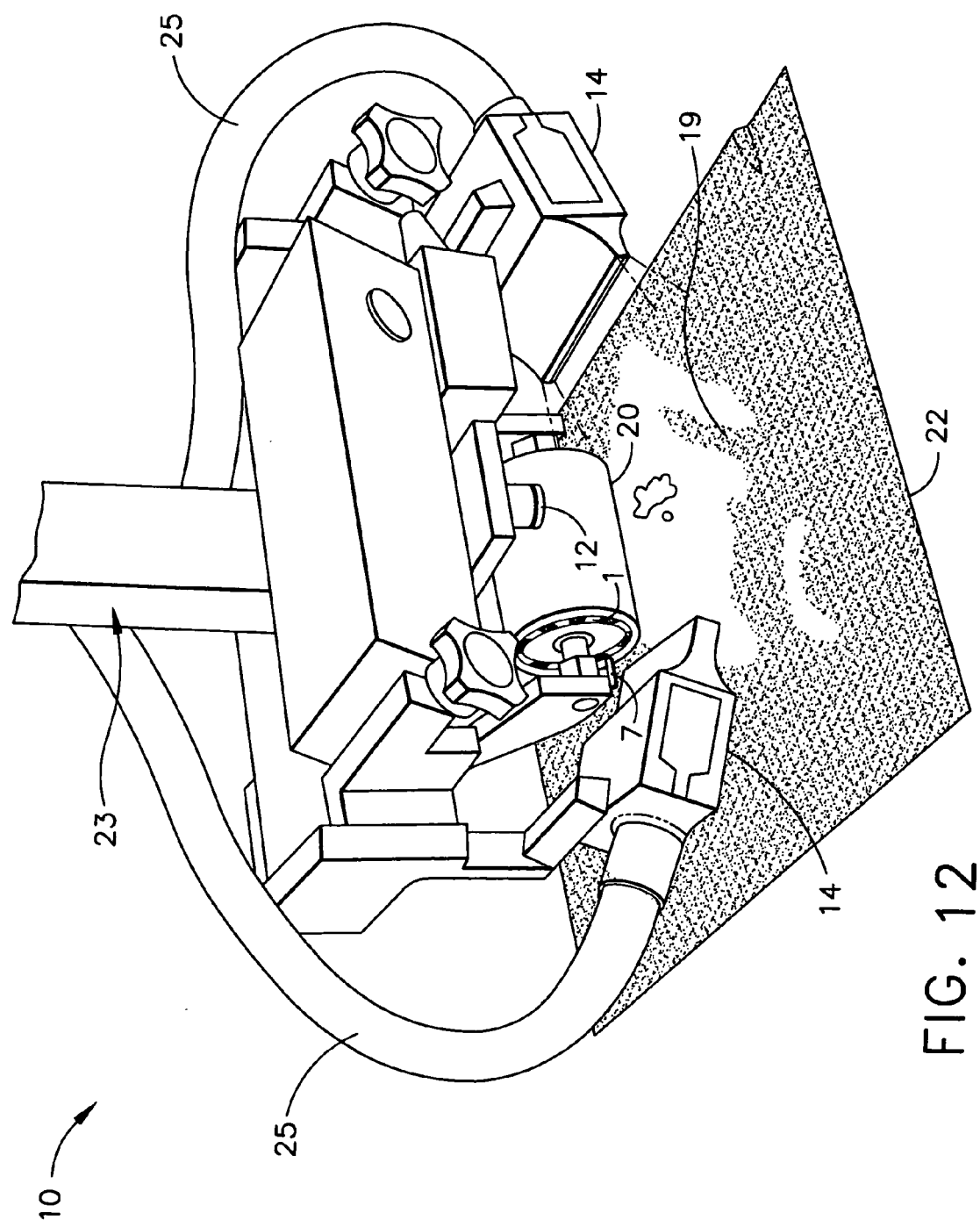
FIG. 12 is a perspective view of another exemplary system for inspecting a composite structure for defects.

Further, the system 10 may include more than one light source. For example, the embodiment of FIG. 10 includes two light sources 14 positioned relative to the composite structure and compaction roller 20 on either side of the reflective surface 16 and camera 12. Another exemplary embodiment that includes two light sources 14 is shown in FIG. 12 in which two linear optical fiber arrays are positioned on opposed sides of the camera 12.

In FIG. 8, the light source 14 is adjustably positioned relative to the composite structure 22 by mounting or attaching the light source 14 to a mounting apparatus 27. The mounting apparatus 27 can include a main shaft 29, a secondary shaft 31, and a locking clamp 33 for quickly and accurately adjusting the position of the light source 14. The mounting apparatus 27, in turn, can be attached to the frame 28, to the camera 12, to the bracket 30, or to some other object that defines a common position for both the light source 14 and the camera 12 such that the light source 14 and camera 12 maintain a constant spatial relationship relative to one another.

The quality and magnitude of the surface illumination of the composite structure can be affected by ambient lighting and by reflectivity of the material. Accordingly, embodiments of the invention advantageously employ an infrared light source to more effectively illuminate dark flaws on a dark background. In this regard, the light source 14 can be selected from an infrared light or another type of light having an infrared component, such as a halogen light source (FIG. 11) or other incandescent light sources (not shown). In other embodiments, the light source 14 can also include a fluorescent light source (e.g., white light LEDs, low pressure/mercury filled phosphor glass tube, etc.), a strobe or stroboscopic light source, a noble gas arc lamp (e.g., xenon arc, etc.), metal arc lamp (e.g., metal halide, etc.) and a lasers (e.g., pulsed lasers, solid state laser diode arrays, infrared diode laser arrays, etc.). The light from the light source 14 may also be pumped from through optical fibers to the point of delivery, such as is shown in FIG. 12.

In some embodiments, the light source 14 is operated at a power level that maximizes, or at least significantly increases, the infrared (IR) component of the light which works well for inspecting dark tow material, such as carbon. In this regard, exemplary power levels in the range of up to about one hundred fifty watts (150W) in the wavelength range of about seven hundred nanometers to eleven hundred nanometers (700 nm–1100 nm) have been sufficient. However, the particular power levels and wavelengths for the light source will likely depend at least in part on the camera's speed and sensitivity, speed at which the material is being laid, delivery losses, and reflectivity of the material being inspected, among other factors. For example, in other embodiments, wavelengths and power levels suitable for inspecting highly reflective materials can be employed.

In the embodiment shown in FIG. 8, the light source 14 may comprise a plurality of LEDs arranged in an array or cluster formation. In one specific embodiment, the light source 14 includes 24 LEDs mounted in an array upon a three-inch square printed circuit board.

Figure 11:
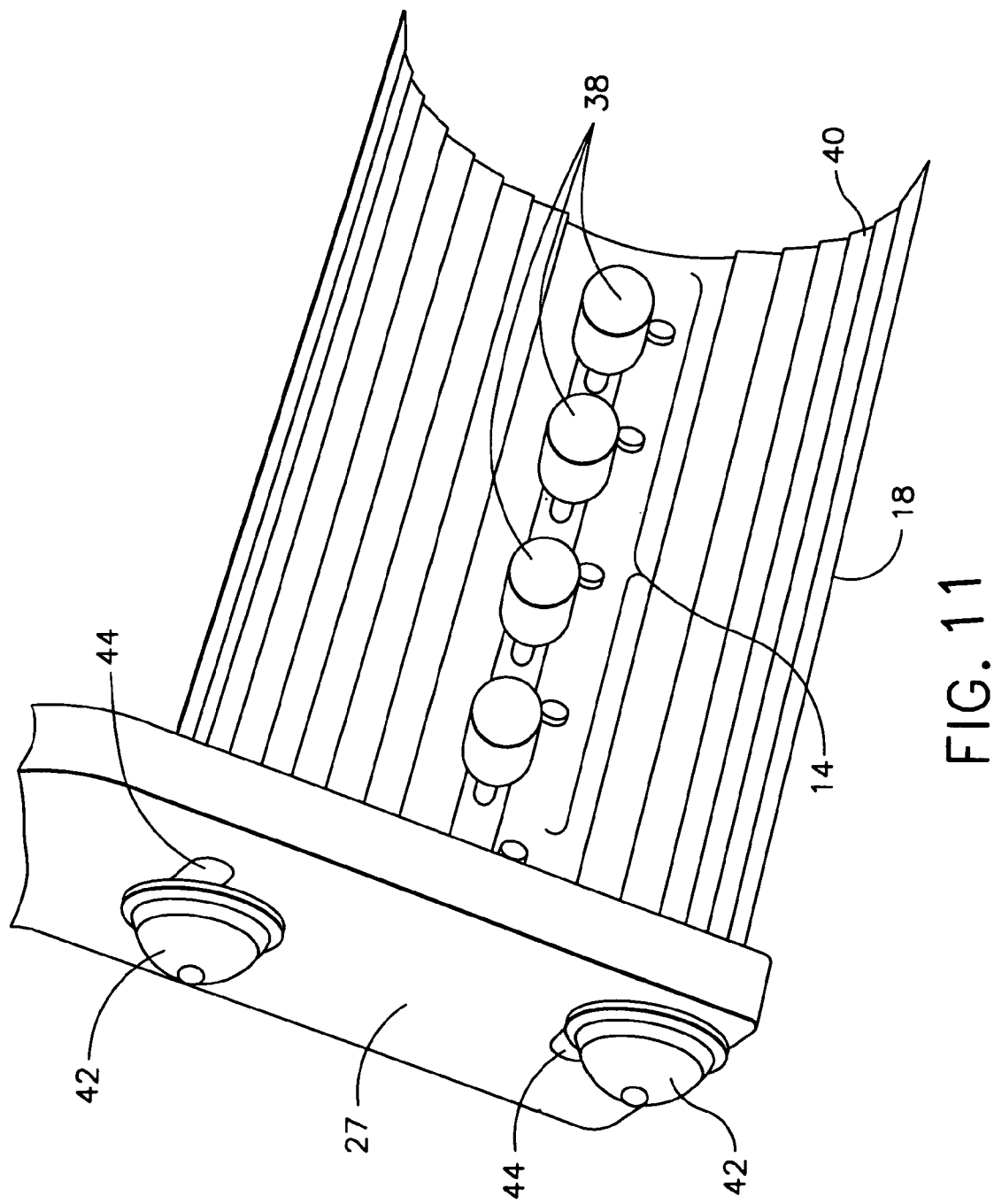
FIG. 11 is a perspective view of a light source according to the system embodiment shown in FIG. 10.

In another embodiment shown in FIGS. 10 and 11, the light source 14 includes four halogen light bulbs 38, although other quantities can and have also been used.

Figure 13:
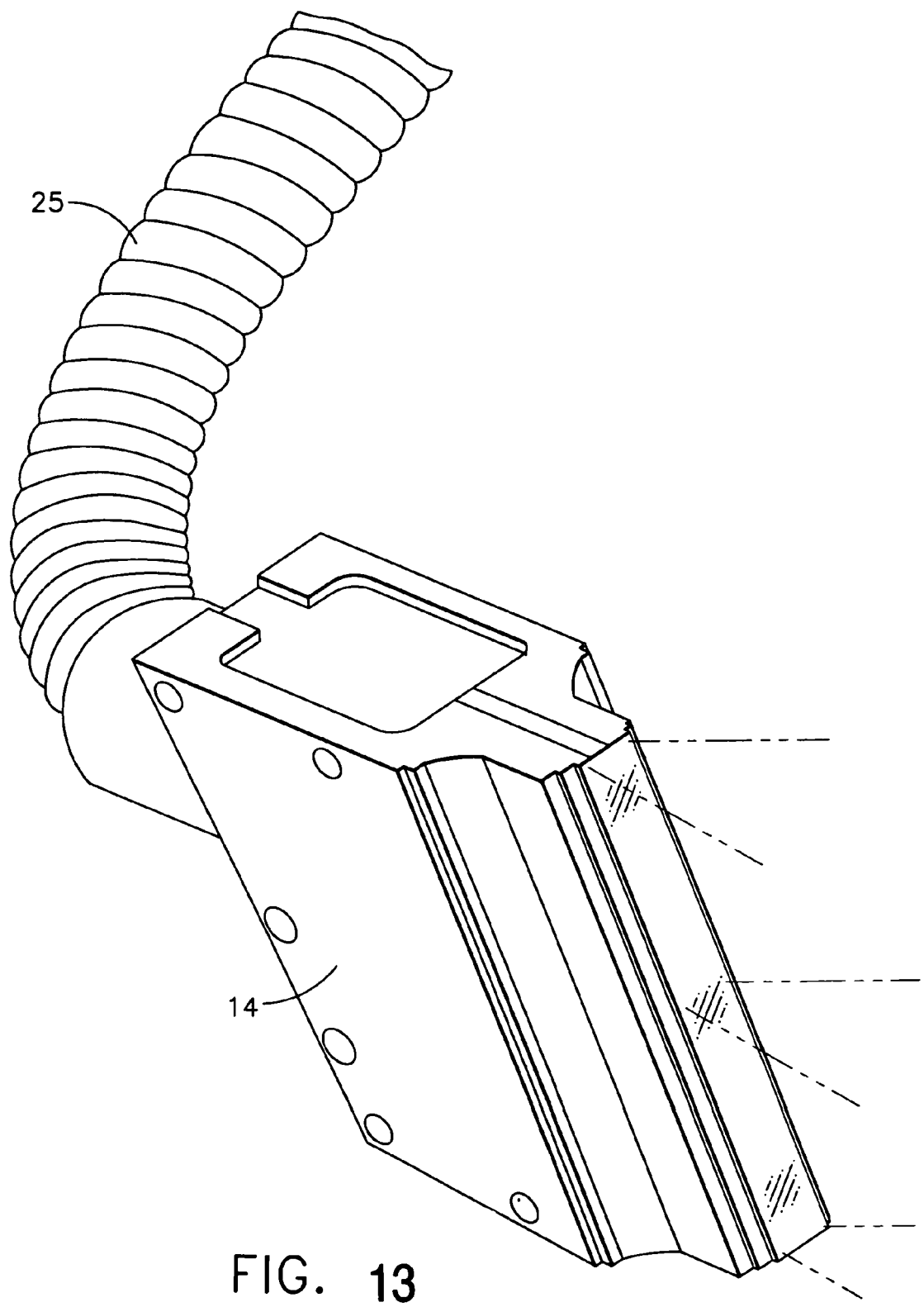
FIG. 13 is a perspective view of a light source according to the system embodiment shown in FIG. 12.
Figure 14:
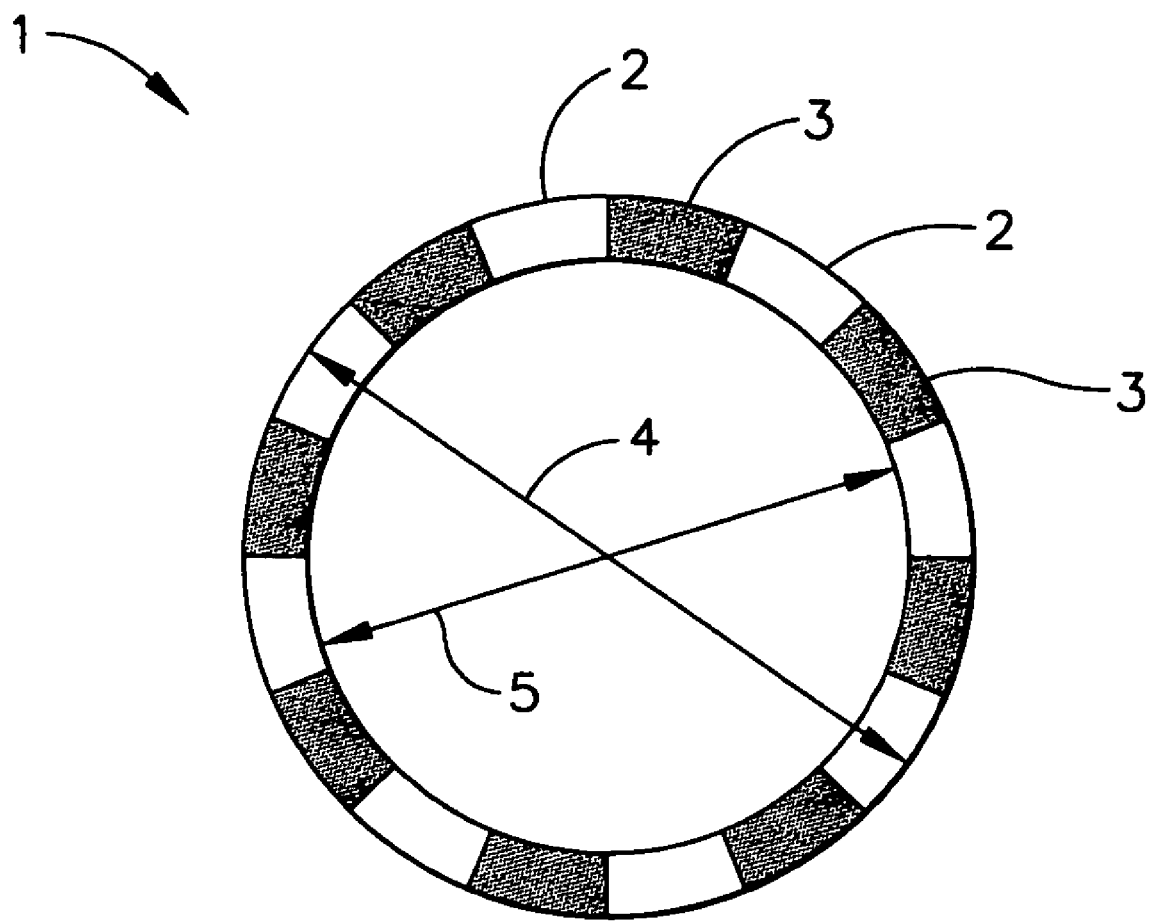
FIG. 14 is a schematic view of the code ring shown in FIG. 9.

In the embodiment shown in FIG. 12, the light source 14 includes two linear optical fiber arrays positioned on opposite sides of the camera 12. The arrays emit light supplied from a remote source (not shown) through an optical fiber bundle 25. An illuminated linear array 14 is shown in FIG. 13.

Referring back to FIG. 10, the system 10 may further include a light reflection element 18 located near the light source 14. The reflection element 18 includes a series of light reflecting surfaces 40 (FIG. 11) that redirect the light towards the desired area to be illuminated. This levels the illumination across the surface and eliminates, or at least substantially reduces, areas of intense light (i.e., hotspots) created by the brightest portion of the light source 14. Hotspots are undesirable because hotspots can prevent consistent illumination of the composite structure, which may lead to errors during the processing of the images captured by the camera 12.

The light reflection elements 40 are particularly advantageous for illuminating curved/contoured surfaces of composite structures because the redirection of the light permits a larger portion of the composite structure to be evenly illuminated.

As shown in FIG. 11, the reflection element 18 is curved around the light source 14, such as in a parabolic shape. On the surface of the reflection element 18 that faces the light source 14, the reflection element 18 includes curved steps 40 substantially parallel to the light source 14. The distance between and curvature of the steps 40 can be chosen to be sufficient to provide even illumination from the sum of the two light sources, one on either side of the region of interest. This enables the reflection element 18 to provide more consistent illumination of the composite structure 22, which prevents, or at least reduces, image processing errors due to inconsistent illumination of the composite structure 22. Alternatively, the shape and/or surface configuration of the reflection element 18 can be modified in other ways that also produce consistent illumination and scattering of the light produced by the light source 14 over the desired portion of the composite structure 22.

In an exemplary embodiment, the reflection element 18 has an overall parabolic shape with seventeen parabolic curved steps 40 having a range of widths from about 0.125 inches at the outer edge of the reflection element 18 to about 0.250 inches at the center of the reflection element 18. The reflection element 18 also has a uniform step height of about 0.116 inches. In other embodiments, however, the reflection element may be provided with different numbers of steps having different uniform or varying widths and different uniform or varying step heights.

Furthermore, the reflection element 18 may be adjusted in order to direct the light produced by the light source 14 and scattered by the reflection element 18 toward the desired portion of the composite structure. For example, as shown in FIG. 11, the reflection element 18 is adjustably mounted to the mounting apparatus 27 with fasteners 42. The loosened fasteners 42 can move within slots 44 to correspondingly adjust the angle of the reflection element 18 relative to the composite structure. Once the reflection element 18 is positioned appropriately, the fasteners 42 are tightened to secure the reflection element 18 in the desired position. Adjustments of the reflection element 18 can also be enabled by other methods, such as by electronic means that permit remote adjustment of the reflection element 18.

It has been observed that the composite structure 22 can produce high glare when illuminated across the direction of placement of the strips 24 but produces substantially less glare when illuminated along the direction of placement of the strips 24. The systems and methods of at least some embodiments exploit the high-glare/low-glare phenomenon by casting light across the top layer of the composite strips 24 in a direction substantially perpendicular to the direction of placement of the strips 24. This produces a relatively large amount of glare on the top layer of the composite structure 22. The underlying layers, which produce significantly less glare than the top layer because of their orientation, will show through any gaps or other defects in the top layer and thus be easily located. In addition, twists and other surface defects in the top layer will alter the orientation of the strips in the top layer and thus correspondingly alter, i.e., decrease, the glare of the top layer at the defect location.

While the high-glare/low-glare phenomenon can occur when illuminated with either visible light or infrared light, the filter 15 used in one embodiment of the system 10 substantially removes the glare caused by ambient light such that only the glare caused by the infrared light source is used to locate the defects. Accordingly, the filter 15 removes the interference of ambient light as the composite structure 22 is being examined for defects.

In any of the system embodiments described herein, there may be one or more cameras 12 and/or one or more light sources 14 with or without reflection elements 18 (collectively referred to as light sources, hereinafter). In addition, the one or more cameras 12 and/or the one or more light sources 14 may be moveable relative to the composite structure. The multiple cameras 12 and/or multiple light sources 14 and the moveability of the camera(s) 12 and/or the light source(s) provides system 10 flexibility in order to capture the most accurate images of the composite structure. Multiple and/or moveable light source(s) 14 permit consistent and sufficient illumination of the desired portion of the composite structure, regardless of the shape of the composite structure. Likewise, multiple and/or moveable camera(s) 12 enable capturing an accurate image of any area of the composite structure, regardless of the shape of the composite structure. As such, the multiple and/or moveable light source(s) and/or camera(s) are particularly advantageous when illuminating and capturing images of curved/contoured portions of composite structures. The multiple and/or moveable light source(s) and/or camera(s) are also advantageous in illuminating and capturing images of composite strips having a width that makes it difficult to illuminate and/or capture images of the entire strip, such that the position of the light source(s) and/or camera(s) may be moved over the entire strip, and/or multiple stationary light source(s) and/or camera(s) may be positioned to cover the entire strip. Systems including moveable cameras and light sources are described in detail in previously referred to U.S. patent application Ser. No. 10/217,805.

The camera 12 and/or the reflective surface 16, which along with the light source 14 and any reflection element 18, can be mounted to the head unit to allow the camera 12 to continuously capture real-time images of the composite structure 22 and the strips 24 as the head unit moves across the composite structure 22 and the composite strips 24 are laid down. If the composite structure 22 is not planar, the inspection point should preferably be as close to the nip point as possible, as described above. If the composite structure 22 is planar, the inspection point can be located further from the placement head unit. In either case, the images can be stored in a memory device 64 for future analysis and/or processed immediately by the processor 66.

The processor 66 may receive the images from the camera 12 or from the memory device 64 in which images have been stored. The processor 66 may then process and analyze the images to facilitate the reliable detection of defects. In at least one embodiment, the processor 66 and memory device 64 are components of a conventional computer.

Various methods can be used to determine the defect locations (e.g., linear distance 19 and lateral distance 21 to a defect 36, FIG. 1) at operation 424 (FIG. 5A). Details regarding systems and methods for determining defect locations are included in previously referred to U.S. patent application Ser. No. 10/726,099.

In an exemplary implementation, linear distance to a defect along a course can be determined by multiplying the velocity of the material placement head unit along the course with the amount of time that has lapsed between when the course began and when the defect is detected.

The start and stop of a course can be determined using signals from the machine load cell which indicate whether or not pressure is being applied to the compaction roller 20 (FIGS. 7, 8, and 10). Receipt of a "pressure on" signal from the machine load cell indicates that the compaction roller 20 is in contact with the composite structure 22 and therefore, that a course has been started. Receipt of a "pressure off" signal indicates that the compaction roller 20 is no longer in contact with the composite structure 22, and therefore that a course has been completed. Accordingly, the time between course start and defect detection can be determined by tracking the amount of time elapsing between receipt of the "pressure on" signal from the machine load cell and the receipt of the signal indicating detection of a defect.

Alternatively, course start and stop can be determined by receipt of a signal from a device employing proximity sensors, lasers, or sound detectors positioned for determining whether or not the compaction roller 20 is in contact with the composite structure 22.

In one implementation, velocity of the head unit is determined by determining the angular velocity of the compaction roller 20 and multiplying the angular velocity by a circumference of the compaction roller 20. Alternatively, other methods can also be used to determine the velocity of the head unit, such as by using a radar gun commonly used for law enforcement purposes in monitoring vehicular speeds along roadways.

Referring to FIGS. 7, 8, and 12, the angular velocity of the compaction roller 20 can be determined by a code ring 1 coupled for common rotation with the compaction roller 20. As shown, the code ring 1 includes alternating contrasting portions 2 and 3, such as alternating black and white segments. In FIG. 12, the code ring 1 includes an outer diameter 4 of about 1.010 inches and an inner diameter 5 of about 0.844 inches, although other ring sizes can also be employed. In other embodiments, the contrasting portions can be provided directly on the compaction roller 20 (e.g., marked on, painted on, etc.), thereby eliminating the need for the separate code ring 1.

With further reference to FIGS. 7 and 8, a photo sensor 7 (e.g., an off-the-shelf photo diode, etc.) is positioned to monitor and capture real-time images of the light-to-dark transitions of the code ring 1 as the code ring 1 rotates along with the compaction roller 20. By detecting and counting the light-to-dark transitions of the ring 1, the compaction roller revolutions can be counted and monitored. The frequency at which the light-to-dark transitions occur can be used to establish the angular velocity of the compaction roller 20. Preferably, axial motion in the compaction roller 20 is minimized in order to maintain the distance from the photo sensor 7 to the code ring 1 constant, which, in turn, allows for more accurate determination of the machine head unit's velocity.

In another exemplary embodiment, the linear distance to a defect along a course can be determined by counting the number (whole and fractional) of revolutions the compaction roller 20 makes from the start of the course to the defect and multiplying that number of revolutions by the circumference of the compaction roller 20. By way of example, the photo sensor 7 and code ring 1 can be used to count the number of revolutions of the compaction roller 20 between receipt of the "pressure on" signal from the machine load cell and receipt of the signal indicating that a defect has been detected.

Various methods can also be employed to determine the lateral distances to defects from the first end 11 of the composite structure 22. See FIG. 1. In one exemplary embodiment, lateral distance to a defect can be calculated by counting the total number of completed courses, not including the course in which the defect resides, and then multiplying the average width of a course by the number of completed courses. This method is particularly effective for tape placement in which each course is the same width, i.e., the width of the tape.

The total number of completed courses can be determined by tracking or counting receipt of the pressure on/off signals from the machine load cell. Receipt of a "pressure on" signal from the machine load cell indicates that the compaction roller 20 is in contact with the composite structure 22 and has thus started a course. Receipt of a "pressure off" signal indicates that the compaction roller 20 is no longer in contact with the composite structure 22 and has thus completed the course.

For fiber placement courses in which the width of each course may not be equal, the lateral distances to defects can be accurately determined by employing a "software ruler." More specifically, the lateral distance can be determined by acquiring a digital image of at least the portion of the composite structure including the lateral distance; selecting a pixel set from the digital image that represents the lateral distance; counting the number of pixels comprising the pixel set; and correlating the pixel count with correlation data (e.g., a predetermined relationship between pixel count and distance) to compute an indirect quantitative measurement for the lateral distance.

Various implementations of the invention are applicable to a wide range of material placement processes, such as fiber placement, tape placement and fabric placement processes, among others. Accordingly, the specific references to fiber placement herein should not be construed as limiting the scope of the present invention to only one specific form/type of material placement process.

While various preferred embodiments have been described, those skilled in the art will recognize modifications or variations which might be made without departing from the inventive concept. The examples illustrate the invention and are not intended to limit it. Therefore, the description and claims should be interpreted liberally with only such limitation as is necessary in view of the pertinent prior art.

What is claimed is:

1. A method for indicating defect locations on a composite structure, the method comprising:
   electronically accessing positional data upon receipt of a defect signal from a defect detection system, the positional data defining a location of a defect on a composite structure;
   determining whether the defect is unacceptable;
   determining whether repair of the defect can be affected using an automated repair system;
   determining whether the defect requires manually affected repair; and
   automatically causing a light source to direct light at the composite structure to indicate:
      the defect location as defined by the positional data;
      whether the defect is unacceptable; and
      if the defect is determined to be unacceptable, at least one of:
         whether repair of the defect can be automatically affected; and
         whether the defect requires manually affected repair.

2. The method of claim 1, wherein the electronically accessing includes extracting the positional data from a part fabrication file, the part fabrication file including numerical control (NC) data for a material placement machine to fabricate the composite structure.

3. The method of claim 2, wherein the electronically accessing includes receiving a signal indicating detection of a defect by an inspection system inspecting the composite structure for defects, and extracting the positional data from the part fabrication file in response to the received signal.

4. The method of claim 3, wherein:
the electronically accessing includes, upon completion of a ply of the composite structure by the material placement machine, accessing the extracted positional data defining defect locations on the completed ply; and
the automatically causing including automatically causing the light source to direct light at the completed ply to indicate the defect locations on the completed ply.

5. The method of claim 1, wherein the automatically causing includes creating a program to automatically generate instructions, in connection with the positional data, for automatically causing the light source to direct light at the composite structure to indicate the defect location.

6. The method of claim 1, wherein the automatically causing includes, upon completion of a ply of the composite structure by a material placement machine, automatically causing the light source to direct light at the completed ply of the composite structure to indicate the defect locations on the completed ply.

7. The method of claim 1, wherein the automatically causing includes automatically causing the light source to direct light at the defect location to illuminate the defect location.

8. The method of claim 1, wherein the light source comprises a laser.

9. The method of claim 8, wherein the automatically causing includes automatically splitting the light emitted by the laser to indicate a plurality of defect locations on the composite structure.

10. The method of claim 1, wherein the automatically causing includes using light to indicate and distinguish among one or more different types of defects.

11. The method of claim 1, wherein the automatically causing includes using light to indicate and distinguish among one or more different categories of acceptance criteria for defects.

12. The method of claim 1, wherein the automatically causing includes having the light source direct light at composite structure to indicate the defect location at least until the defect at the defect location is repaired.

13. The method of claim 1, wherein the automatically causing includes indicating one or more defect locations within a region on the composite structure by having the light source direct light to indicate the region.

14. A system for indicating defect locations on a composite structure, the system comprising:
at least one light source;
a controller associated with the light source to control operation of the light source;
a computer-readable media including instructions executable by the controller for:
electronically accessing positional data upon receipt of a defect signal from a composite structure inspection system, the positional data defining a location of a defect on a composite structure;
determining whether the defect is unacceptable;
determining whether repair of the defect can be affected using an automated repair system;
determining whether the defect requires manually affected repair; and
automatically generating instructions for automatically causing the controller to operate the light source such that the light source directs light at the composite structure to indicate:
the defect location as defined by the positional data;
whether the defect is unacceptable; and
if the defect is determined to be unacceptable, at least one of:
whether repair of the defect can be automatically affected; and
whether the defect requires manually affected repair.

15. The system of claim 14, wherein the computer-readable media further includes instructions executable by the controller for extracting the positional data from a part fabrication file including numerical control (NC) data for a material placement machine to fabricate the composite structure.

16. The system of claim 15, wherein the computer-readable media further includes instructions executable by the controller for receiving a signal indicating detection of a defect by an inspection system inspecting the composite structure for defects, and wherein the positional data is extracted from the part fabrication file in response to the received signal.

17. The system of claim 16, wherein the computer-readable media further includes instructions executable by the controller for:
accessing, upon completion of a ply of the composite structure by the material placement machine, the extracted positional data defining defect locations on the completed ply; and
wherein the controller operates the light source such that the light source directs light at the completed ply to indicate the defect locations on the completed ply.

18. The system of claim 14, wherein the controller operates the light source, upon completion of a ply of the composite structure by a material placement machine, such that the light source directs light at the completed ply to indicate the defect locations on the completed ply.

19. The system of claim 14, wherein the light source comprises a laser.

20. The system of claim 19, further comprising a light-splitting device to split the light emitted by the laser to indicate a plurality of defect locations on the composite structure.

21. The system of claim 14, wherein the computer-readable media further includes instructions executable by the controller for communicating with a material placement machine fabricating the composite structure.

22. A computer-readable media having stored thereon instructions executable by a processor for:
electronically accessing positional data upon receipt of a defect signal from a composite structure inspection system, the positional data defining a location of a defect on a composite structure;
determining whether the defect is unacceptable;
determining whether repair of the defect can be affected using an automated repair system;
determining whether the defect requires manually affected repair; and
automatically generating instructions for automatically causing a light source to direct light at the composite structure to indicate:
the defect location as defined by the positional data;
whether the defect is unacceptable; and
if the defect is determined to be unacceptable, at least one of:
whether repair of the defect can be automatically affected; and
whether the defect requires manually affected repair.

23. The program of claim 22, wherein the computer-readable media further has stored thereon instructions executable by the controller for extracting the positional data from a part fabrication file, the part fabrication file including numerical control (NC) data for a material placement machine to fabricate the composite structure.

24. The program of claim 23, wherein the computer-readable media further has stored thereon instructions executable by the controller for receiving a signal indicating detection of a defect by an inspection system inspecting the composite structure for defects, and wherein the positional data is extracted from the part fabrication file in response to the received signal.

25. The program of claim 24, wherein the computer-readable media further has stored thereon instructions executable by the controller for accessing, upon completion of a ply of the composite structure by the material placement machine, the extracted positional data defining defect locations on the completed ply, and wherein the instructions automatically cause the light source to direct light at the completed ply to indicate the defect locations on the completed ply.

26. The program of claim 22, wherein the computer-readable media further has stored thereon instructions executable by the controller for communicating with a material placement machine fabricating the composite structure.

* * * * *

UNITED STATES PATENT AND TRADEMARK OFFICE
CERTIFICATE OF CORRECTION

PATENT NO.        : 7,193,696 B2
APPLICATION NO. : 10/822538
DATED             : March 20, 2007
INVENTOR(S)       : Engelbart et al.

It is certified that error appears in the above-identified patent and that said Letters Patent is hereby corrected as shown below:

On Title Page

Item 73
The assignee on the above-referenced issued patent should read:

The Boeing Company
100 North Riverside Plaza
Chicago, Illinois 60606-1596

Signed and Sealed this

Twenty-seventh Day of November, 2007

JON W. DUDAS
*Director of the United States Patent and Trademark Office*

UNITED STATES PATENT AND TRADEMARK OFFICE
CERTIFICATE OF CORRECTION

PATENT NO. : 7,193,696 B2  Page 1 of 1
APPLICATION NO. : 10/822538
DATED : March 20, 2007
INVENTOR(S) : Engelbart et al.

It is certified that error appears in the above-identified patent and that said Letters Patent is hereby corrected as shown below:

On Title page

Item 73
The assignee on the above-referenced issued patent should read:

The Boeing Company
100 North Riverside Plaza
Chicago, Illinois 60606-1596

Signed and Sealed this

Eighteenth Day of December, 2007

JON W. DUDAS
*Director of the United States Patent and Trademark Office*